(12) United States Patent
Xia

(10) Patent No.: US 12,011,515 B2
(45) Date of Patent: Jun. 18, 2024

(54) BONEGRAFT SUBSTITUTE AND METHOD OF MANUFACTURE

(71) Applicant: 3D-BGS (UK) Limited, Swansea (GB)

(72) Inventor: Zhidao Xia, Swansea (GB)

(73) Assignee: 3D-BGS (UK) LIMITED, Swansea (GB)

(*) Notice: Subject to any disclaimer, the term of this patent is extended or adjusted under 35 U.S.C. 154(b) by 35 days.

(21) Appl. No.: 16/981,643

(22) PCT Filed: Mar. 21, 2019

(86) PCT No.: PCT/GB2019/050795
§ 371 (c)(1),
(2) Date: Sep. 16, 2020

(87) PCT Pub. No.: WO2019/180439
PCT Pub. Date: Sep. 26, 2019

(65) Prior Publication Data
US 2021/0106719 A1    Apr. 15, 2021

(30) Foreign Application Priority Data

Mar. 22, 2018 (GB) ..................................... 1804594

(51) Int. Cl.

| | |
|---|---|
| *A61L 27/18* | (2006.01) |
| *A61L 27/02* | (2006.01) |
| *A61L 27/12* | (2006.01) |
| *A61L 27/32* | (2006.01) |
| *A61L 27/54* | (2006.01) |
| *A61L 27/56* | (2006.01) |
| *A61L 27/58* | (2006.01) |
| *B33Y 70/10* | (2020.01) |
| *B33Y 80/00* | (2015.01) |

(52) U.S. Cl.
CPC ............. *A61L 27/12* (2013.01); *A61L 27/025* (2013.01); *A61L 27/32* (2013.01); *A61L 27/54* (2013.01); *A61L 27/56* (2013.01); *A61L 27/58* (2013.01); *B33Y 70/10* (2020.01); *B33Y 80/00* (2014.12); *A61L 2300/414* (2013.01); *A61L 2400/12* (2013.01); *A61L 2430/02* (2013.01)

(58) Field of Classification Search
CPC ........ A61L 27/12; A61L 27/025; A61L 27/32; A61L 27/54; A61L 27/56; A61L 27/58; A61L 2300/414; A61L 2400/12; A61L 2430/02; A61L 2300/406; A61L 2300/41; A61L 2300/416; B33Y 70/10; B33Y 80/00; B33Y 10/00; B33Y 70/00
See application file for complete search history.

(56) References Cited

U.S. PATENT DOCUMENTS

| | | | |
|---|---|---|---|
| 9,827,268 B2 * | 11/2017 | Hatanaka | ................. A61K 6/54 |
| 2004/0254668 A1 | 12/2004 | Jang et al. | |
| 2005/0217538 A1 | 10/2005 | Reinstorf et al. | |

FOREIGN PATENT DOCUMENTS

| | | | | |
|---|---|---|---|---|
| CN | 101366971 A | | 2/2009 | |
| CN | 104771785 A | * | 7/2015 | |
| CN | 105749337 A | | 7/2016 | |
| CN | 107469152 A | * | 12/2017 | ........... A61L 27/446 |
| EP | 0 395 187 A2 | | 10/1990 | |
| EP | 3 031 441 A1 | | 6/2016 | |
| NZ | 561209 A | * | 12/2010 | ............. A61L 27/46 |
| WO | WO-2017031899 A1 | * | 3/2017 | |

OTHER PUBLICATIONS

Trombetta et al. Annals of biomedical engineering 45.1 (2017): 23-44. (Year: 2017).*
Shao et al. 2017 Biofabrication 9, 025003 (Year: 2017).*
Fernandez et al., "Production and characterization of new calcium phosphate bone cements in the $CaHPO_4$-$\alpha$-$Ca_3(PO_4)_2$ system: pH, workability and setting times," *J Mater Sci Mater Med*. 10:223-230, 1999.
GB 1804594.8 Search Report mailed Sep. 25, 2018 (4 pages).
PCT/GB2019/050795 International Search Report and Written Opinion mailed Jun. 25, 2019 (15 pages).

* cited by examiner

*Primary Examiner* — Mina Haghighatian
*Assistant Examiner* — Janice Y Silverman
(74) *Attorney, Agent, or Firm* — Klarquist Sparkman, LLP

(57) ABSTRACT

The invention concerns a method of making a synthetic, biodegradable, bone graft comprising a three-dimensional porous structure; a formulation of constituents for use in said method; a synthetic, biodegradable bone graft produced by said method; and a method of surgery comprising use of said bone graft.

10 Claims, 19 Drawing Sheets

BONEGRAFT SUBSTITUTE AND METHOD OF MANUFACTURE

CROSS REFERENCE TO RELATED APPLICATIONS

This is the U.S. National Stage of International Application No. PCT/GB2019/050795, filed Mar. 21, 2019, which was published in English under PCT Article 21(2), which in turn claims the benefit of Great Britain Application No. 1804594.8, filed Mar. 22, 2018.

FIELD OF THE INVENTION

The invention concerns a method of making a synthetic, biodegradable, bone graft comprising a three-dimensional porous structure; a formulation of constituents for use in said method; a synthetic, biodegradable bone graft produced by said method; and a method of therapy/surgery comprising use of said bone graft.

BACKGROUND OF THE INVENTION

Bone defects caused by bone tumour, diseases and trauma are a great challenge to orthopaedic surgery and material scientists. Such bone defects result in a void in the bone structure. Bone generally can regenerate completely but, unless the defect space is very small it requires some form of scaffold to support it during growth. The repair of bone defects therefore requires a void filling material that must be capable of supporting bone regeneration at the defective site. Bone tissue regeneration requires bioactive scaffolds, or bone graft substitutes, to guide functional osteoblastic cells that will deposit new bone matrix for bone formation. The porous structure of the scaffold, which mimics bone structure, is crucial to the success of bone regeneration.

The most suitable material for a bone graft is bone tissue harvested from the patients themselves. This is referred to as an autologous or autogenous bone graft. However, there are significant challenges in obtaining an autologous bone graft from the patient. Firstly, the available donor sites within a patient from which an autologous bone graft may be harvested are limited. In addition, the harvesting of the autologous bone graft requires additional surgery. It has been shown that such surgery can cause morbidity at the donor site.

Allograft bone grafts represent an alternative and they can be stored in bone banks for later use, unfortunately however, the availability of allograft bone grafts is not only limited but they also carry the potential risk of disease transmission by viruses or bacteria.

As an alternative to an autologous bone graft, it is known to use materials of a biological origin to create a bone graft substitute, typically in a process referred to as xenogenic bone grafting. Substrates such as bovine porous demineralized bone or demineralized bone matrix (DBM) may be used. However, these materials also present a risk of disease transfer as well as an immunological response when implanted in the patient. Deprotonation and defatting having been employed to reduce the antigenic response, but this has been shown to be at the cost of the osteo-inductive capacity of the material.

Synthetic, calcium-based bone graft substitutes (BGS), such as bioactive glass ceramics, calcium phosphate ceramics (hydroxyapatite (HA), beta-tricalcium phosphate (TCP) or biphasic calcium phosphate) are currently available for clinical use. These materials are biocompatible and osteo-conductive. In use, the materials have been shown to guide the regenerating bone tissue from the periphery of the defect toward the centre of the graft to fill and regenerate the defect, although the full success rate of these materials in terms of regeneration has yet to be achieved. This is partially because connective pores and porous structures are essential for effective bone formation, however, ceramics are generally brittle, and so these materials do not lend themselves to providing porous structures without compromising their mechanical properties. Furthermore, and problematically, many of these materials are not biodegradable. For example, hydroxyapatite ceramics are non-biodegradable: β-tricalcium phosphate (Beta-TCP) shows very little absorption at 3-4 years following implantation in clinical trials. Non- or slow-biodegradable bone grafts potentially risk the generation of stress forces due to the differences in the mechanical properties between the graft and host bone tissue and this may result in a fracture. Further, residual non-biodegradable bone grafts in the body can be a source of bacterium biofilm formation in the event of infection.

It is known to use coral as a bone graft substitute. Hard corals are formed by innumerable individual polyps that are cemented together by the calcium carbonate 'skeletons' they secrete. Coral has a structure that is similar to the structure of cancellous bone. Coral is also biocompatible, as well as osteoconductive and resorbable, it also allows for the complete regeneration of bone structure. However, commercially available coral is restricted in many parts of the world, it is in limited supply, it is very slow to grow, and as a result it is very expensive. U.S. Pat. No. 8,936,638 uses a technique to farm coral in a special environment with added nutrients, such as silicium, calcium silicate, magnesium and phosphate to enhance bone formation once the coral is harvested and processed. However, it is a very long process before the farmed coral is ready for application.

It is therefore apparent that current bone graft substitutes are not fully satisfactory due to one or all pf the following factors: (1) limited resources; (2) allergy or disease transmission; (3) optimal pore sizes and connective porous structure; (4) suitable mechanical properties and/or (5) controllable biodegradation property. There is therefore an unmet need for a bone graft substitute for use in bone damage repair and reconstruction, that can biodegrade over time leaving only the regenerated bone in its place. It is also important that the material can biodegrade without leaving any toxic residues within the patient. At the same time, the material must remain structurally viable for a period suitably long to enable the bone to fully regenerate. As such, the period of biodegradation is important in addition to the biodegradability itself.

Accordingly, we herein disclose an improved bone graft substitute and a method of making same using a three-dimensional printing process which addresses the above described problems, and/or which offers improvements generally. We have unexpectedly found that using a mixture of inorganic and organic compositions having a given viscosity, we can form a biodegradable bone substitute that mimics coralline hydroxyapatite/calcium carbonate. We have also found that the scaffold is nontoxic to populating cells such as human mesenchymal stem cells (hMSCs), biocompatible to tissue and can repair bone defect through conductive osteogenesis. Further, through modification of the composition, the biodegradation of the bone scaffold can be carefully controlled, in addition to the mechanical properties of same. Finally, through the method of manufacture—a printing process—the pore size can be carefully controlled and defined.

STATEMENTS OF INVENTION

According to a first aspect of the invention there is provided a method for making a synthetic, biodegradable, bone graft substitute comprising:
(a) mixing, in any order, calcium carbonate; a binding material and a wetting agent and/or a gelling agent to make a cement or slurry, wherein the binding material comprises at least a first component and a second component that react in the presence of at least said wetting agent and/or gelling agent to provide a cement or slurry; and
(b) exuding or compressing the cement or slurry of part (a) into a shape suitable for functioning as a bone graft.

In a preferred method of the invention the following steps are executed in the specified order:
(a) mixing calcium carbonate with a binding material to provide a powdered mixture, wherein the binding material comprises at least a first component and a second component that react in the presence of a wetting agent and/or a gelling agent to provide a cement or slurry;
(b) mixing the powdered mixture of part (a) with a wetting agent and/or a gelling agent to make a cement or slurry;
(c) printing a three-dimensional bone graft substitute (3D-BGS) from the cement or slurry of part (b) onto a platform using a three-dimensional printer.

Reference herein to 3D printing, also called additive manufacturing (AM) and Rapid Prototyping, includes techniques such as bioprinting, selective laser sintering and fused deposition modelling (FDM). These techniques enable the production of a complex, solid or hollow structural component based on 3D Computer Aided Design (CAD) model. The 3D printing process allows components to be produced rapidly and without the need of tooling.

In a preferred embodiment the three-dimensional printer is preferably a bioprinter. A bioprinter comprises a syringe that pushes a mixture through a nozzle under controlled conditions to build up a three-dimensional structure. Bioprinting, uses equipment such as a 3D bio-plotter, by injecting a paste, gel, cement or slurry from a nozzle which then hardens to form a 3D structure. A 3D bioprinter can be used to print porous scaffolds with selected mechanical properties. A 3D bioprinter can be used to print porous scaffolds with selected mechanical properties. Advantageously, compared to other printing processes, it has been found that when using bioprinting there is no sintering or melting required and the process enables careful control of connective pores and desired pore sizes in the structure. It has also surprisingly been found that an increase in mechanical strength is achieved using bioprinting.

As will be appreciated by those skilled in the art, calcium carbonate can be obtained from numerous sources and may be used in the method according to the invention. In a preferred embodiment, calcium carbonate may be naturally occurring or synthetically manufactured. Most ideally, said calcium carbonate is obtained from a natural source such as, but not limited to, cuttlefish bone. The use of cuttlefish bone provides a cheap and non-exhaustive source of substrate material that provides chemical and structural properties similar to that of bone and coral when combined with the binding material.

In yet a further preferred embodiment, said calcium carbonate is provided as a powder.

It has been found that the relative amount of calcium carbonate is important for determining the biodegradation profile of the bone graft substitute, with it found that the higher the amount of calcium carbonate as a proportion of the end product the faster the biodegradation. Further, and importantly, the relative amount of calcium carbonate is imperative to the mechanical strength of the resultant bone graft substitute, with insufficient amounts leading to disintegration of the product. Conversely, when the amount of calcium carbonate present in excessive amounts the cement cannot be printed or leads to defective graft formation. Therefore, in even yet a further preferred embodiment, the amount of calcium carbonate is provided in the range 10-60% by weight of the cement, including every 0.1% therebetween. It has been found within this range the cement can be easily printed and leads to a mechanically stable resultant bone graft substitute. More ideally, the amount of calcium carbonate is provided in the range 20-50% by weight of the cement, including every 0.1% therebetween.

In yet a further preferred embodiment, the calcium carbonate may be in the form of micro or nanoparticles. As will be appreciated by those skilled in the art, reference herein to micro or nanoparticles refers to particles of calcium carbonate less than 1000 microns or less than 1 micron in diameter, respectively. In a preferred embodiment, said microparticles are in the range of 1-30 µm, including every 1 µm integer therebetween Preferably, nanoparticles are used. The utilisation of nanoparticles has been found to increase the mechanical strength of the 3D-BGS. More preferably, the nanoparticles are in the range of about 1-999 nm in diameter, yet more preferably 10-999 nm, including every 1 nm integer therebetween. More preferably still, said nanoparticles are in the range of about 10-500 nm, including every 1 nm integer therebetween. Most ideally, said nanoparticles are in the range of about 50-250 nm, including every 1 nm integer therebetween.

Reference herein to a binding material refers to a material having at least a first component or chemical compound and at least a second component or chemical compound that react together when in the presence of solution/water that enables the calcium carbonate particles to bind to each other and to solidify and form a porous 3D-BGS.

Advantageously, it has been found that in this arrangement, the binding material is able to bind the calcium carbonate and provide for improved mechanical strength of the 3D-BGS. This is particularly beneficial for a bone graft substitute as fragility is significantly reduced whilst maintaining the beneficial properties of biodegradability. Thus, the risk of damage to the structure, inside or outside, the body is significantly reduced.

In a preferred embodiment, said first component comprises a first calcium phosphate, and the second component comprises a second calcium phosphate, wherein said first calcium phosphate of the first component has a higher ratio of calcium to phosphate (Ca/P ratio) than the second calcium phosphate of the second component. In this manner, the first and second components react to produce hydroxyapatite (HA), or calcium phosphate cement (CPC).

In a preferred embodiment, said first and second calcium phosphate is selected from the group comprising:
tetracalcium phosphate ($Ca_4(PO_4)_2O$; TTCP);
tricalcium phosphate ($2Ca_3(PO_4)_2$; TCP);
calcium hydrogen phosphate ($CaHPO_4$);
calcium dihydrogen phosphate ($Ca(H_2PO_4)_2$; CDHP);
dicalcium phosphate dehydrate ($CaHPO_4 \cdot 2H_2O$; DCP), or
octacalcium phosphate ($Ca_8H_2(PO_4)_6 \cdot 5H_2O$; OCP).

More ideally, said first and second calcium phosphate is selected from the group comprising:
tetracalcium phosphate ($Ca_4(PO_4)_2O$; TTCP);
tricalcium phosphate ($2Ca_3(PO_4)_2$; TCP);
calcium hydrogen phosphate ($CaHPO_4$);

calcium dihydrogen phosphate ($Ca(H_2PO_4)_2$; CDHP);
dicalcium phosphate dehydrate ($CaHPO_4 \cdot 2H_2O$; DCP), or
octacalcium phosphate ($Ca_8H_2(PO_4)_6 \cdot 5H_2O$; OCP) provided when said first calcium phosphate is TCP said second calcium phosphate is not DCP and vice versa.

More ideally, said first calcium phosphate is tetracalcium phosphate ($Ca_4(PO_4)_2O$; TTCP) and said second calcium phosphate is selected from the group comprising:
tricalcium phosphate ($2Ca_3(PO_4)_2$; TCP);
calcium hydrogen phosphate ($CaHPO_4$);
calcium dihydrogenphosphate ($Ca(H_2PO_4)_2$; CDHP);
dicalcium phosphate dehydrate ($CaHPO_4 \cdot 2H_2O$; DCP), or
octacalcium phosphate ($Ca_8H_2(PO_4)_6 \cdot 5H_2O$; OCP).

Most ideally, said first calcium phosphate is tetracalcium phosphate ($Ca_4(PO_4)_2O$; TTCP) and said second calcium phosphate is selected from the group comprising:
calcium hydrogen phosphate ($CaHPO_4$);
calcium dihydrogenphosphate ($Ca(H_2PO_4)_2$; CDHP),
dicalcium phosphate dehydrate ($CaHPO_4 \cdot 2H_2O$; DCP), or
octacalcium phosphate ($Ca_8H_2(PO_4)_6 \cdot 5H_2O$; OCP).

Advantageously, according to this preferred embodiment, TTCP can react with one or more calcium phosphates (with lower Ca/P ratio) to form hydroxyapatite without the formation of acids or bases as by-products of the reaction, for example, according to the following equations:

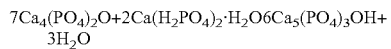

$$7Ca_4(PO_4)_2O + 2Ca(H_2PO_4)_2 \cdot H_2O \rightarrow 6Ca_5(PO_4)_3OH + 3H_2O$$

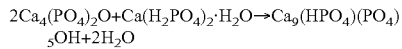

$$2Ca_4(PO_4)_2O + Ca(H_2PO_4)_2 \cdot H_2O \rightarrow Ca_9(HPO_4)(PO_4)_5OH + 2H_2O$$

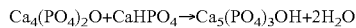

$$Ca_4(PO_4)_2O + CaHPO_4 \rightarrow Ca_5(PO_4)_3OH + 2H_2O$$

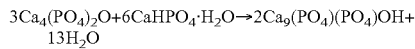

$$3Ca_4(PO_4)_2O + 6CaHPO_4 \cdot H_2O \rightarrow 2Ca_9(PO_4)(PO_4)OH + 13H_2O$$

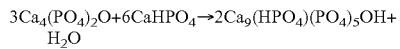

$$3Ca_4(PO_4)_2O + 6CaHPO_4 \rightarrow 2Ca_9(HPO_4)(PO_4)_5OH + H_2O$$

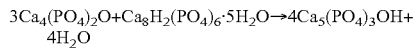

$$3Ca_4(PO_4)_2O + Ca_8H_2(PO_4)_6 \cdot 5H_2O \rightarrow 4Ca_5(PO_4)_3OH + 4H_2O$$

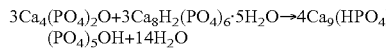

$$3Ca_4(PO_4)_2O + 3Ca_8H_2(PO_4)_6 \cdot 5H_2O \rightarrow 4Ca_9(HPO_4)(PO_4)_5OH + 14H_2O$$

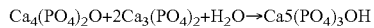

$$Ca_4(PO_4)_2O + 2Ca_3(PO_4)_2 + H_2O \rightarrow Ca_5(PO_4)_3OH$$

In a preferred embodiment, the binding material comprising the first and second components is provided in the range 10-50% by weight of the cement, including every 0.1% therebetween. Most ideally, the amount of calcium carbonate is provided in the range 25-40% by weight of the cement, including every 0.1% therebetween.

In yet a further preferred embodiment still, the first and second components are provided in solid form and are mixed and ground together in relative amounts wherein the ratio of the first component to the second component is a range of about 0.5 to 5.5, more preferably a ratio of about 1 to 1.5. It has been found that the relative ratios of the first and second components are important to the mechanical strength and structural integrity of the bone graft substitute, which are variable, given the desired strength varies according to the intended purpose of the bone graft.

In order to enable exudation or injection from the bio-printer the mixture must be capable of flowing. Thus, in a preferred embodiment, the product is in the form of a paste or slurry. The mixture may also be termed a colloid as it exhibits properties in between a solid and a liquid.

Additionally, parts (a) above may further comprise mixing of an additive wherein said additive is any compound that affects viscosity and so ensures the mixed product has suitable fluidity to flow but not so much that it fails to hold shape when exuded or compressed. This also affects mechanical strength and setting time and so viscosity has to controlled with this in mind. In a preferred embodiment, said additive is selected from the group comprising: gelatin, collagen, cellulose, self-assembling peptides or a bioink. Most ideally, said additive is gelatin and thus also satisfies the requirement of being a gelling agent.

In yet a further preferred embodiment still, said additive is provided in a solution or solvent, most ideally in water.

It has further been found that the relative proportion of additive is important for the fluidity of the product. Accordingly, in yet a further preferred embodiment said additive is provided in the range 10-50% by weight of the cement, including every 0.1% therebetween. More ideally, the amount of additive is provided in the range 25-50% by weight of the cement, including every 0.1% therebetween. Most ideally, the amount of additive is provided in the range 25-40% by weight of the cement, including every 0.1% therebetween.

In yet a further preferred embodiment still, the mixing in step (a), and preferred step (b), with the wetting agent or gelling agent is preferably undertaken at a temperature in the range of 10° C. and 60° C., including every 0.1° C. integer therebetween. Such a temperature range is beneficial to maintain the desired viscosity of the mixture whilst also ensuring that the binding material does not unintentionally set through the temperature becoming too high. More preferably, a temperature of between 20 and 60° is used, including every 0.1° C. integer therebetween. Yet more preferably, a temperature of between 25 and 40° is used, including every 0.1° C. integer therebetween. Even more preferably the temperature range is between 30-37° C., including every 0.1° C. integer therebetween. This ensures that the mixture is in the optimised thermal window for ensuring viscosity whilst also ensuring that, once deposited, setting occurs quickly thereby maintaining the desired shape of the exuded, compressed or printed structure.

In even yet a further preferred embodiment still, the method includes providing a platform onto which the 3D-BGS is exuded, compressed or printed wherein the temperature of the platform is selected such that the reaction speed of the first and second components is reduced whilst also ensuring that the gelatin cools to facilitate the provision of the optimised and preferred shape to the structure. A suitable temperature range for the platform is between 1° C.-40° C., more preferably between 2.5° C.-10° C., including every 0.1° C. integer therebetween.

In yet a further preferred embodiment still, the printing of step (c) comprises depositing the mixture from step (b) layer by layer to produce 3D-BGS wherein each layer is ideally deposited at an angle with respect to the preceding layer to generate a porous structure, most ideally said angle is about 90° between each layer. The resulting 3D-BGS is formed having a porous structure in which a 3D matrix of pores are interconnected with each other. These pores form interconnected tunnels creating a structure like cancellous bone.

Most ideally, the printing of step (c) is controlled to produce desired pore sizes in the 3D-BGS product wherein said pore sizes are selected according to the intended use. In a preferred embodiment, step (c) produces pore sizes between 1-1000 μm, including every 1 μm integer therebetween. Most preferably, the pore sizes are between 200-750 μm, including every 1 μm integer therebetween.

In yet a further preferred embodiment still, step (c) further comprises printing onto a substrate comprising a support material wherein said cement is deposited in a manner such that said support material is incorporated, partially or fully, into the 3D-BGS. As will be appreciated by those skilled in the art, said support material may further enhance the mechanical properties of the 3D-BGS, such as further improved mechanical strength, which may be appropriate in circumstances wherein the bone graft is used in tissues or bones of the body that are subjected to high mechanical stress. Examples of such support materials include, but are not limited to, carbon nanotubes, natural or synthetic polymer micro-fibres such as poly-L-lactide (PLA) or silk fibroin.

In certain applications, it may desirable to produce a bone graft substitute that releases an active agent such that when incorporated into the body the active agent is released into the surrounding tissue. Examples of such active agents include pharmaceutical agents and drugs in particular small drug molecules as well as biomacromolecules, biological agents including growth/maturation factors and agents known to promote bone and cartilage generation, reduce or remove risk of infection, or prevent abnormal cell growth, such as, but not limited to, growth factors (e.g. bone morphogenic protein, BMPs; PDGF, FGF, EGF etc.), antibiotics (e.g. gentamycin and vancomycin for osteomyelitis) anti-inflammatory/anti-bone resorption agents (e.g. bisphosphonates), steroidal drugs, anti-cancer therapeutics (e.g. Denosumab, Cisplatin, and Paclitaxel). As will be appreciated by those skilled in the art, dependent upon the nature of the active agent to be included, the active agent may be incorporated into the cement, slurry or product prior to the exuding, compressing or printing step, for example, via its incorporation into the mixture of steps (a). Advantageously, as the method does not require the need for extreme temperatures or setting agents, there is no detriment to the activity of the active agent during the manufacturing process. Alternatively, in certain circumstances the active agent may be incorporated into the cement, slurry or product during or following step (b) or (c).

It has been found that calcium carbonate scaffolds have a relatively fast biodegradation rate that is not best suited to a bone graft product. Therefore, in a further preferred embodiment, the method further comprises a final step (c or d) wherein the calcium carbonate is converted to calcium phosphate, or coated with calcium phosphate, and most preferably hydroxyapatite (HA) which is the natural bone mineral composition and has a much slower rate of biodegradation. The conversation of the calcium carbonate to converted to HA may be conducted following the exuding, compressing or printing steps.

In one embodiment the calcium carbonate may be converted to HA using hydrothermal transformation, which in one embodiment follows the equation:

$$10CaCO_3 + 6(NH_4)2HPO_4 + 2H_2O \rightarrow Ca_{10}(PO_4)_6(OH)_2 + 6(NH_4)_2CO_3 + 4H_2CO_3$$

In the hydrothermal transformation process the 3D-BGS is soaked in a 0.6 mol/ml ammonium dihydrogen phosphate solvent in a reactor, then reacted at 120° C. for 2 to 16 hours, including every 1 hour integer therebetween Following this chemical reaction, the scaffolds are washed with deionised water and thoroughly remove any un-reacted ammonium dihydrogen and then dried in an oven at a temperature below between 37-60° C., including every 0.1° C. integer therebetween. The chemical reaction which occurs during autoclaving transforms the calcium carbonate to calcium phosphate, in the form of HA. The length of time autoclaving is selected to vary the degree of transformation. Preferably the autoclaving time is selected to achieve partial conversion in which some but not all the calcium carbonate is converted to HA. It has been found that HA has a ceramic structure and as a result the biodegradation rate of HA is undesirably slow, and so full conversion of the scaffold to HA is not desired. Instead partially conversion of calcium carbonate to calcium phosphate is preferred, with the degree of conversion being controlled to achieve the desired biodegradation rate of the 3D-BGS.

Alternatively, 3D-BGS may be coated with HA post formation. HA may be fabricated using a simulated body fluid (SBF), which is a solution with an ion concentration close to that of human blood plasma. The 3D-BGS is immersed in the SBF solvent at a temperature of approximately 37° C. The ion concertation of the SBF solvent is $Na^+$ 142.0, $K^+$ 5.0, $Ca^{2+}$ 2.5, $Mg^{2+}$ 1.5, $Cl^-$ 147.8, $HCO_3^-$ 4.2, $HPO_4^{2-}$ 1.0, $SO_4^{2-}$ 0.5 (in mM). The SBF is buffered at pH 7.4 by a buffer e.g. tris-hydroxymethyl-aminomethane (Tris, 50 mM) and hydrochloric acid having a ratio of 1 M-HCl 40 ml/L and $(CH_2OH)_3CNH_2$ 6.057 g/L. The 3D-BGS remains immersed in the SBF for period of between 1 day and 14 days. More specifically, the period of immersion may be varied to control to the degree of HA transformation between 1 and 7 days, including every 0.5 day therebetween.

According to a second aspect of the invention, there is provided a mixture for making a three-dimensional bone graft scaffold comprising calcium carbonate and a binding material wherein the binding material comprises a first component and a second component that react in the presence of wetting agent and/or gelling agent to provide a cement or slurry.

In preferred embodiment, said mixture comprises calcium carbonate in an amount provided in the range 10-60% by weight of the cement, including every 0.1% therebetween. It has been found at this amount the cement can be easily printed and lead to a mechanically stable resultant bone graft substitute. More ideally, the amount of calcium carbonate is provided in the range 20-50% by weight of the cement, including every 0.1% therebetween.

In a preferred embodiment, said first and second calcium phosphate is selected from the group comprising:
tetracalcium phosphate ($Ca_4(PO_4)_2O$; TTCP);
tricalcium phosphate ($2Ca_3(PO_4)_2$; TCP);
calcium hydrogen phosphate ($CaHPO_4$);
calcium dihydrogen phosphate ($Ca(H_2PO_4)_2$; CDHP);
dicalcium phosphate dehydrate ($CaHPO_4 \cdot 2H_2O$; DCP), or
octacalcium phosphate ($Ca_8H_2(PO_4)_6 \cdot 5H_2O$; OCP).

More ideally, said first and second calcium phosphate is selected from the group comprising:
tetracalcium phosphate ($Ca_4(PO_4)_2O$; TTCP);
tricalcium phosphate ($2Ca_3(PO_4)_2$; TCP);
calcium hydrogen phosphate ($CaHPO_4$);
calcium dihydrogen phosphate ($Ca(H_2PO_4)_2$; CDHP);
dicalcium phosphate dehydrate ($CaHPO_4 \cdot 2H_2O$; DCP), or
octacalcium phosphate ($Ca_8H_2(PO_4)_6 \cdot 5H_2O$; OCP) provided when said first calcium phosphate is TCP said second calcium phosphate is not DCP and vice versa.

More ideally, said first calcium phosphate is tetracalcium phosphate ($Ca_4(PO_4)_2O$; TTCP) and said second calcium phosphate is selected from the group comprising:
tricalcium phosphate ($2Ca_3(PO_4)_2$; TCP);
calcium hydrogen phosphate ($CaHPO_4$);
calcium dihydrogenphosphate ($Ca(H_2PO_4)_2$; CDHP);
dicalcium phosphate dehydrate ($CaHPO_4 \cdot 2H_2O$; DCP), or
octacalcium phosphate ($Ca_8H_2(PO_4)_6 \cdot 5H_2O$; OCP).

Most ideally, said first calcium phosphate is tetracalcium phosphate ($Ca_4(PO_4)_2O$; TTCP) and said second calcium phosphate is selected from the group comprising:

calcium hydrogen phosphate ($CaHPO_4$);
calcium dihydrogenphosphate ($Ca(H_2PO_4)_2$; CDHP),
dicalcium phosphate dehydrate ($CaHPO_4 \cdot 2H_2O$; DCP), or
octacalcium phosphate ($Ca_8H_2(PO_4)_6 \cdot 5H_2O$; OCP).

According to a third aspect of the invention, there is provided a three-dimensional bone graft substitute (3D-BGS) comprising calcium carbonate and a porous scaffold that is cancellous-like in structure and coated, partially or fully, with hydroxyapatite (HA).

In preferred three-dimensional bone graft substitute (3D-BGS), said calcium carbonate is provided in an amount in the range 10-60% by weight, including every 0.1% therebetween. It has been found at this amount the cement can be easily printed and lead to a mechanically stable resultant bone graft substitute. More ideally, the amount of calcium carbonate is provided in the range 20-50% by weight, including every 0.1% therebetween.

According to a fourth aspect of the invention, there is provided a method of treating bone loss comprising inserting into a bone or attaching to a bone a 3D-BGS according to the invention.

Preferred features of each aspect of the invention may be as described in connection with any of the other aspects.

Throughout the description and claims of this specification, the words "comprise" and "contain" and variations of the words, for example "comprising" and "comprises", mean "including but not limited to" and do not exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

All references, including any patent or patent application, cited in this specification are hereby incorporated by reference. No admission is made that any reference constitutes prior art. Further, no admission is made that any of the prior art constitutes part of the common general knowledge in the art.

Other features of the present invention will become apparent from the following examples. Generally speaking, the invention extends to any novel one, or any novel combination, of the features disclosed in this specification (including the accompanying claims and drawings). Thus, features, integers, characteristics, compounds or chemical moieties described in conjunction with a particular aspect, embodiment or example of the invention are to be understood to be applicable to any other aspect, embodiment or example described herein, unless incompatible therewith.

Moreover, unless stated otherwise, any feature disclosed herein may be replaced by an alternative feature serving the same or a similar purpose. The Invention will now be described by way of example only with reference to the Examples below and to the following Figures wherein:

BRIEF SUMMARY OF THE DRAWINGS

FIG. 7A: hMSCs grew on the scaffold with 38% percentage by weight $CaCO_3$. FIG. 7B: hMSCs grow on the scaffold with 46% percentage by weight $CaCO_3$. FIG. 7C: hMSCs grow on the scaffold with 30% percentage by weight $CaCO_3$;

FIG. 16A: the dark coloured area shows implanted 3D-BGS, light grey areas are new trabecular bone formation, and the blue areas are toluidine blue stained cells in bone marrow (containing lipid droplets), blood vessels and bone tissue. The 3D-BGS implants are completely integrated and firmly bond to new trabecular bone tissue. The majority of 3D-BGS was degraded and replaced by new bone formation. FIG. 16B: High magnification of FIG. 16A shows a large particle of biodegrading 3D-BGS within new formed trabecular bone tissue. The scattered small Toluidine blue stained dots are osteocytes; whereas the large Toluidine Blue areas are bone marrow (containing lipid droplets) and new blood vessels. FIG. 16C: High magnification of the marked area in FIG. 16B. Toluidine blue stained dots with canaliculus are osteocytes; whereas the large Toluidine Blue area is new blood vessel. FIG. 16D: The high electron density crystalline showing by backscatter demonstrated where the 3D-BGS particles are. The white arrows indicated osteocytes lacunae. The osteocytes are closely integrated with 3D-BGS.

Figure 1:
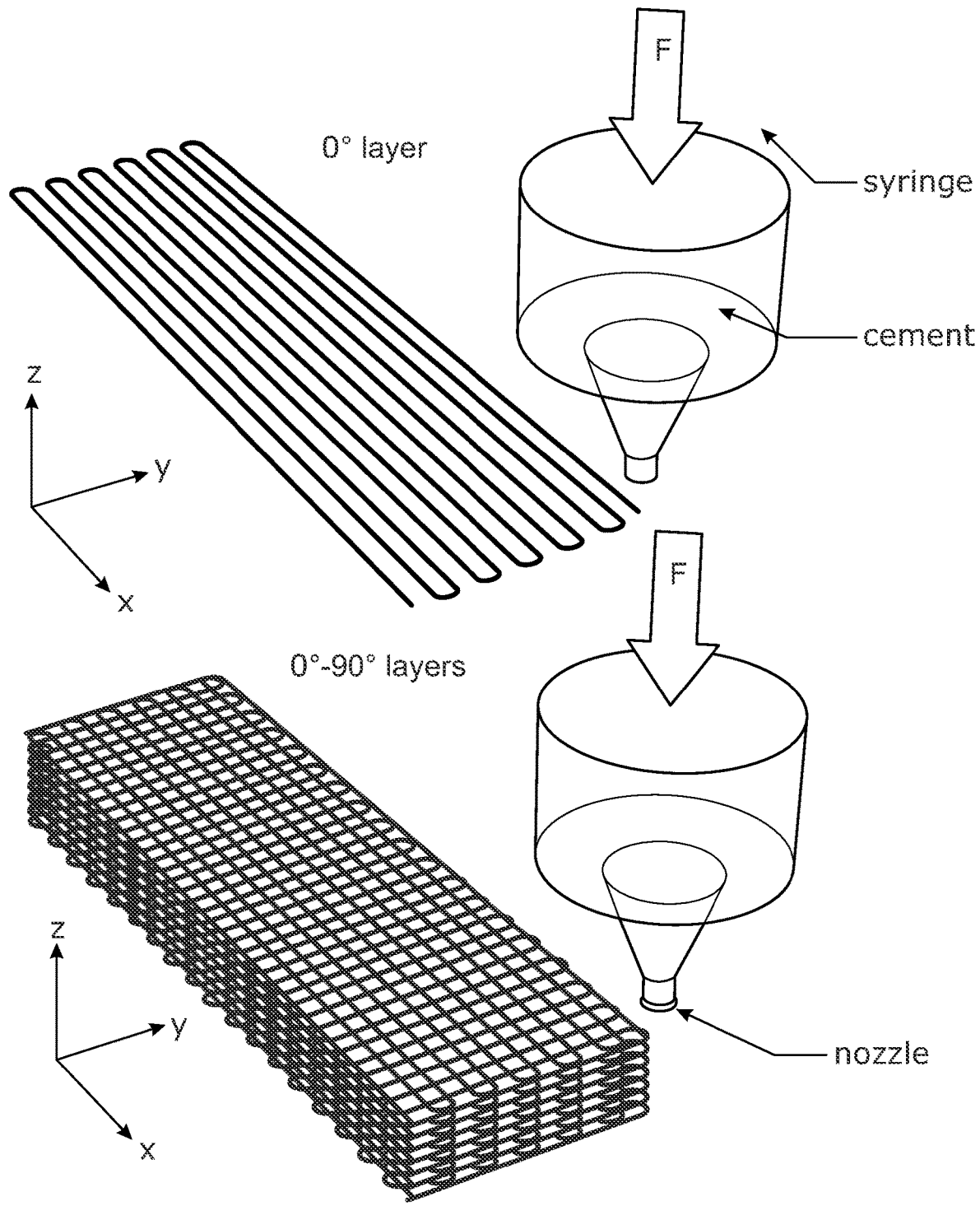
FIG. 1 shows a schematic representation of a bioprinter for use in the production of a structure according to an illustrative embodiment of the present invention.

Table 1. Parameters of the lab based bioplotter used in printing;

Table 2. Proportions of gelatin and $CaCO_3$ in each test at room temperature, gelatin solvent is 35% (percentage by weight) in the cement;

Table 3. Proportions of gelatin and $CaCO_3$ in each test at 32° C., gelatin solvent is 42% (percentage by weight) in the cement;

Table 4. Proportions of gelatin and $CaCO_3$ in each test at 37° C., gelatin solvent is 35% (percentage by weight) in the cement;

Table 5. Feasibility test of different percentage by weight gelatin solvent (15% concentration) with a fixed powder component (0.388 g $CaHPO_4$, 0.612 g TTCP and 1 g $CaCO_3$);

Table 6. Weight by percentage of each component in an example 3D-BGS

Table 7. The proportion of remaining high crystalline implants in backscatter image Materials and Methods Materials Gelatin from bovine skin was supplied by Sigma-Aldrich; Gelatin powder was supplied by Merk KGaA Germany; hMSC was isolated from bone from patient with informed consent and ethic approval by South-Wales Research Ethic Committee (REC reference: 12/WA/0029); Alamarblue and LIVE/DEAD® Viability/Cytotoxicity Kit was supplied by Thermal Fisher-Life Technology; TTCP (tetracalcium phosphate) was supplied by Shanghai Rebone Biomaterials Co., Ltd; Calcium hydrogen phosphate was supplied by Shanghai Rebone Biomaterials Co., Ltd; Calcium Carbonate (99%) was supplied by Sigma-Aldrich.

Feasibility Study

Different proportions of calcium Carbonate, TTCP and Calcium hydrogen phosphate were mixed together following the formula:

$$Ca_4(PO_4)_2O + CaHPO_4 \xrightarrow{H_2O} Ca_5(PO_4)_3OH$$

and were grinded for 20 minutes. Different concentrations of gelatin solvent was made by mixing gelatin powder and double stilled water and was left in oven overnight by 37° C. The mixed powder and gelatin solvent was well mixed manually in 37° C. environment. The cement (mixture of powders and solvent) was transferred into syringe and cement was pressed to check if it can come out and stand to hold a structure. Cement setting time was also test by mixing TTCP, calcium hydrogen phosphate and double stilled water together, mixtures were leaving in 4% and 37° C. The mixtures were checked if they are agglomerated every 2 minutes.

Viscosity Test

Gelatin solvent was taken out and loaded on the platform of rotonetic 2 drive (Bohlin Gemini HR). Viscosity and gel transmission temperature was tested using a 20 mm clamp, and testing temperature was 25-37° C.

3D Printing Process

Calcium Carbonate, TTCP and Calcium hydrogen phosphate was mixed together and was grinded for 20 minutes. Gelatin solvent was made by mixing the powder and deionised water and was left in oven overnight by 37° C. The mixed powder and gelatin solvent was well mixed manually in 37° C. environment. The paste (mixture of powders and solvent) was transferred into syringe. A 2.5 mm diameter metal nozzle was loaded. The scaffold was built by Bioplotter manufacturer series (EnvisionTec), the parameters are shown in Table 1.

FTIR

Calcium carbonate, TTCP, Calcium hydrogen phosphate, gelatin, pure hydroxyapatite and 3D printed scaffolds were tested by FT-IR spectrometer (PerkinElmer UATR Two) with a spectral resolution of 4 $cm^{-1}$.

Cytotoxicity (hMSC)

hMSC isolated from the bone of the patients were seeded into T75 flasks and keep them in incubator until about 75% of the flask was covered by cells and cells were cultured into next passage. The media were replaced every 3 days. After 10 days, the cells were seeded on the scaffold which had been washed by PBS twice and immersed in alpha MEM overnight for Alamarblue assay and Live/Dead staining.

Alamarblue Assay

Wells with scaffolds and cells were washed by PBS twice and were soaked in Alamarblue solvent which made up with 5% Alamarblue and 95% media in incubator for 2 hours. Alamarblue solvent was transferred into the black 96 well plate after 2 hours, the results were shown by the microplate reader (BMH LABTECH, series number: 415-1387).

Live/Dead Staining

Wells with scaffolds and cells were washed in PBS twice and were soaked in the Live/Dead dye which made up following the ratio PBS 2 ml, Calcein AM 1 μL, EthD-1 2 μL and Hechst 33324 5 μL in incubator for 15 minutes. Cells were washed by PBS twice after stained. Results were shown on confocal microscopy (ZEISS LSM 710).

Scanning Electron Microscopy (SEM) Observation

The surface structure of coralline hydroxyapatite/calcium carbonate (CHACC) and 3D BGS before and after incorporating hMSCs for 2 weeks were observed by SEM. In brief, at the end of 2 weeks culture of hMSCs on CHACC and 3D BGS, the materials were fixed in 4% glutaraldehyde in 0.1M PBS, dehydrated in a serial of ethanol, the ethanol was replaced by 50% and 100% hexamethldisilizane, air-dried, sputter-coated with gold and observed by SEM.

Juxtapositional Implantation Between Tibia and Tibialis Anterior Muscle in Rats Adult Waster rats (6-8 weeks) were intraperitoneally injected with chloral hydrate at 400 mg/kg for anaesthesia; laid at supine position. The front legs were shaved and a 5-7 mm incision between tibia and tibialis anterior muscle was carefully produced without damaging periosteum on the tibia. The subcutaneous facia was dissected to expose tibia and tibialis anterior muscle, and a 2 mm×2 mm×2 mm (1) clinically applied gelatin sponge; (2) 3D BGS; and (3) 3D BGS containing 10% bioglass were implanted juxtapositionally between tibia and tibialis anterior muscle. The wound was stitched subcutaneously then the fully layer of skin and cleaned with povidone iodine to avoid infection. Analgesia was used for two days. The procedure was approved by local ethical committee at Tongji Medical School, Huazhong University of Science and Technology.

Three weeks after operation, the rats were euthanized by schedule 1 procedure and the autopsies were harvested and fixed immediately in 4% glutaraldehyde 0.1 M PBS. Then the materials were serially dehydrated in ethanol, embedded in resin. Decalcified semi-thin sections were produced for toluidine blue staining and ultrathin sections for transmission electron microscopy.

Bone Regeneration in Rat Femoral Defect Model

Adult Waster rats (6-8 weeks) were intraperitoneally injected with chloral hydrate at 400 mg/kg for anaesthesia; laid at supine position. The left front legs were shaved and a 10 mm incision along lateral patellar tendon was carefully produced without damaging periosteum on the femur. The patella was dislocated to expose the femur. A 5 mm×φ3.5 mm intercondylar bone defect was created using a dental drill, and groups of 5 mm×φ3.5 mm (1) clinically applied gelatin sponge; (2) 3D BGS was implanted in the defect. The patella was relocated and the patellar ligament and subcutaneous ligament were stitched then the full thickness skin. The wounds were cleaned with povidone iodine to avoid infection. Analgesia was used for two days. The procedure was approved by local ethical committee at Tongji Medical School, Huazhong University of Science and Technology. At 1, 2 and 3 months after operation, the rats were euthanized by schedule 1 procedure and the left distal femur containing the implants were harvested and fixed immediately in neutral 10% formalin. The autopsies were scanned by a MicroCT to illustrate the bone defect regeneration; then serially dehydrated in ethanol, embedded in resin. Decalcified semi-thin sections were produced for toluidine blue staining and ultrathin sections for transmission electron microscopy.

MicroCT

The bone defects were scanned by a MicroCT (Scanco VivaCT40). The data set was collecting using 70 kV voltage, 21 μm layer thickness and 200 ms scanning speed.

Gross Observation

The gross images were obtained from the sawed samples.

Sectioning and Toluidine Blue Staining 10 mm thick sections were cut on a Leica RM2155 motorised microtome with a tungsten knife, and flattened by placing on a drop of isopropanol, overlaying with cling film and rolling with a cylindrical steel rod.

For light microscopy, sections were stained with 1% toluidine blue in 50 mM Tris buffer pH 7.3 The sections were examined with an Olympus BX51 research light microscope (Olympus Optical Co. (U.K.) Ltd, London, U.K) and digital photomicrographs captured with a Zeiss Axiocam and Axiovision software (Carl Zeiss Vision GmbH, Hallbergmoos, Germany).

TEM

For TEM, selected areas of blocks were sawn out, re-embedded in LR White resin and 100 nm sections were cut with a glass knife on an Ultracut E ultramicrotome and collected onto 300 mesh nickel grids. All sections were stained with uranyl acetate and lead citrate. For TEM, sections were examined in a Philips CM12 TEM (FEI U. K. Ltd. UK) at 80 kV and images captured with a Megaview III camera and AnalySIS software (Soft Imaging System GmbH, Germany).

Results

Manufacturing of 3D-BGS

One of the most important elements for a 3D-BGS made by a bioplotter is if the cement can flow out of the nozzle easily. Feasibility was tested at room temperature (27° C.), 32° C. and 37° C. At room temperature, the cement mixture with 10-14% gelatin concentration was liquid-like; cements with 15-19% were more viscous and worked well for the first 4 minutes; cements with 20-25% gelatin were gel-like and could not pass through the nozzle. At 32° C., cements with 10-14% gelatin concentration were fluid; cements with 15-19% were more viscous and worked well for the first 10 minutes; cements with 20-25% gelatin were gel-like and could not pass through the nozzle. At 37° C., cement with 10-14% gelatin concentration was fluid; cements with 15-19% were more viscous and worked well during the entire duration; cements with 20-25% gelatin were sufficiently fluid but found to have limited duration of use only for the first 2 minutes. The results are shown in tables 2, 3 and 4.

Cement feasibility test of gelatin percentage by weight versus temperature was tested. 33%-36% percentage by weight of gelatin works well at all temperatures. The result is shown in table 5. Cement setting time is 40 minutes at 37° C., 1 hour at room temperature and 2 hours at 4° C.

Viscosity Test

Figure 2:
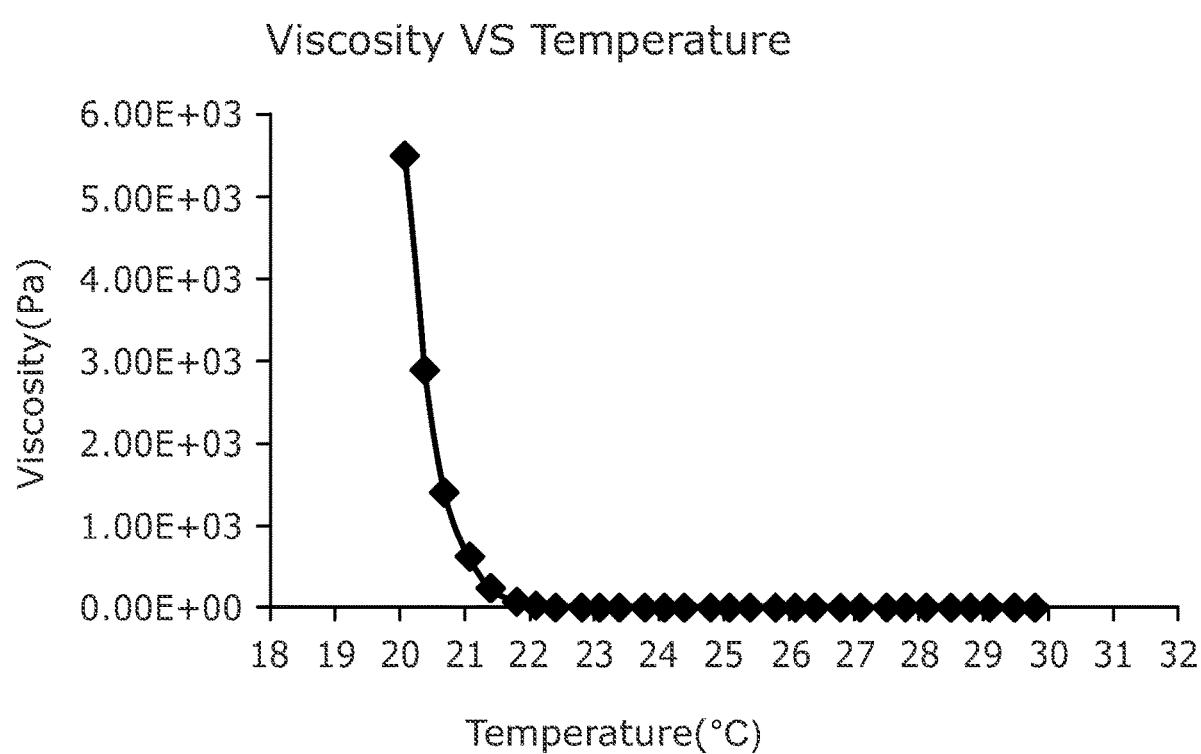
FIG. 2 shows a graph of gelatin viscosity as a function of temperature.

Gelatin solvent is fluid when its temperature is above 30° C., so viscosity was assessed from 20° C. to 30° C. As shown in FIG. 2 the viscosity changes at about 22° C., thus gelatin with 15% concentration changes from fluid to gel at this temperature (FIG. 2).

3D Printing Process

Figure 3A:
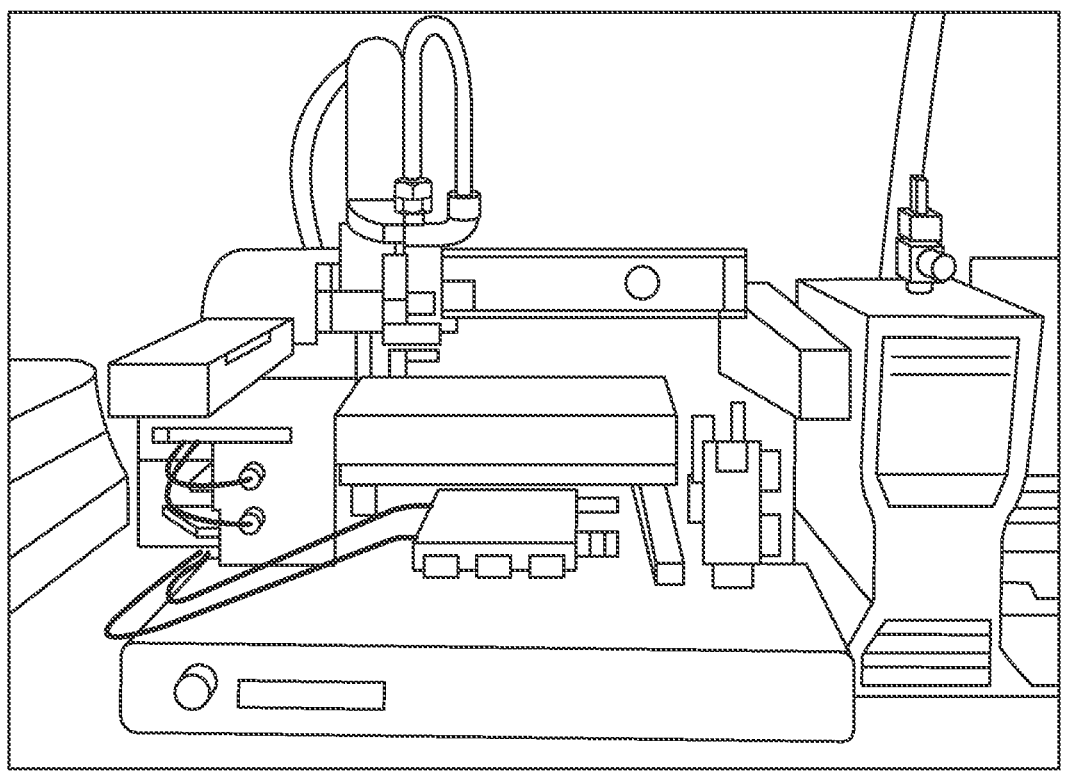
FIG. 3A shows a bioplotter for 3D printing and FIG. 3B shows an example of 3D-BGS made by the bioplotter.
Figure 3B:
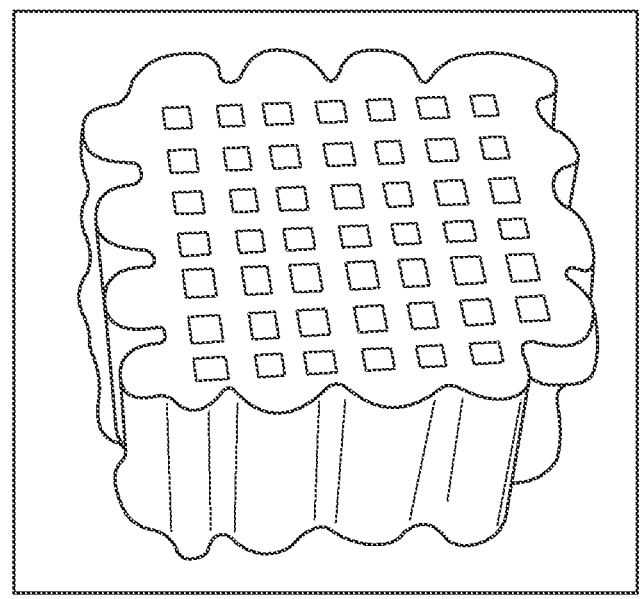

Cement was mixed and printed by bioplotter following the parameters showed in table 6. The testing model is shown in FIG. 3.

XRD

Figure 11:
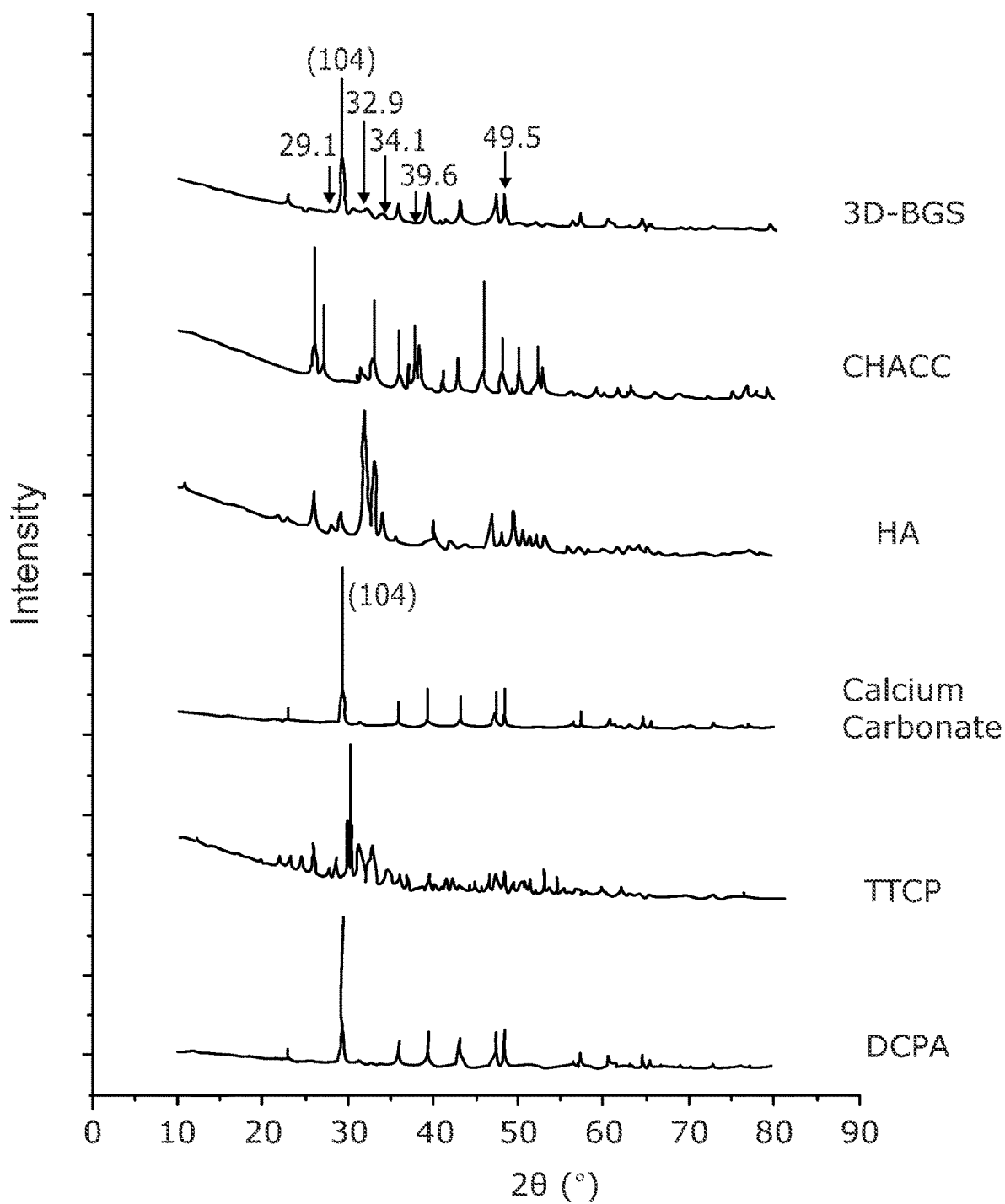
FIG. 11. X-ray diffraction analysis (XRD) analysis of hydroxyapatite (HA), coralline hydroxyapatite/calcium carbonate (CHACC), 3D-BGS and calcium carbonate. In the XRD patterns of the 3D-BGS, the diffraction peaks of calcium carbonate in the 3D-BGS are still visible. More importantly, the diffraction peaks of hydroxyapatite (HA) appear at 2θ values of 29.1°, 32.9°, 34.1°, 39.6° and 49.5° which correspond to (002), (211), (300), (130) and (213) planes, respectively. These diffraction peaks are in a good agreement with the diffraction standard data of pure HA (JCPDS PDF #09-0432)

In FIG. 11, the XRD patterns of the 3D-BGS, the diffraction peaks of calcium carbonate in the 3D-BGS are still visible. More importantly, the diffraction peaks of hydroxyapatite (HA) appear at 2θ values of 29.1°, 32.9°, 34.1°, 39.6° and 49.5° which correspond to (002), (211), (300), (130) and (213) planes, respectively. These diffraction peaks are in a good agreement with the diffraction standard data of pure HA (JCPDS PDF #09-0432)

Figure 4:
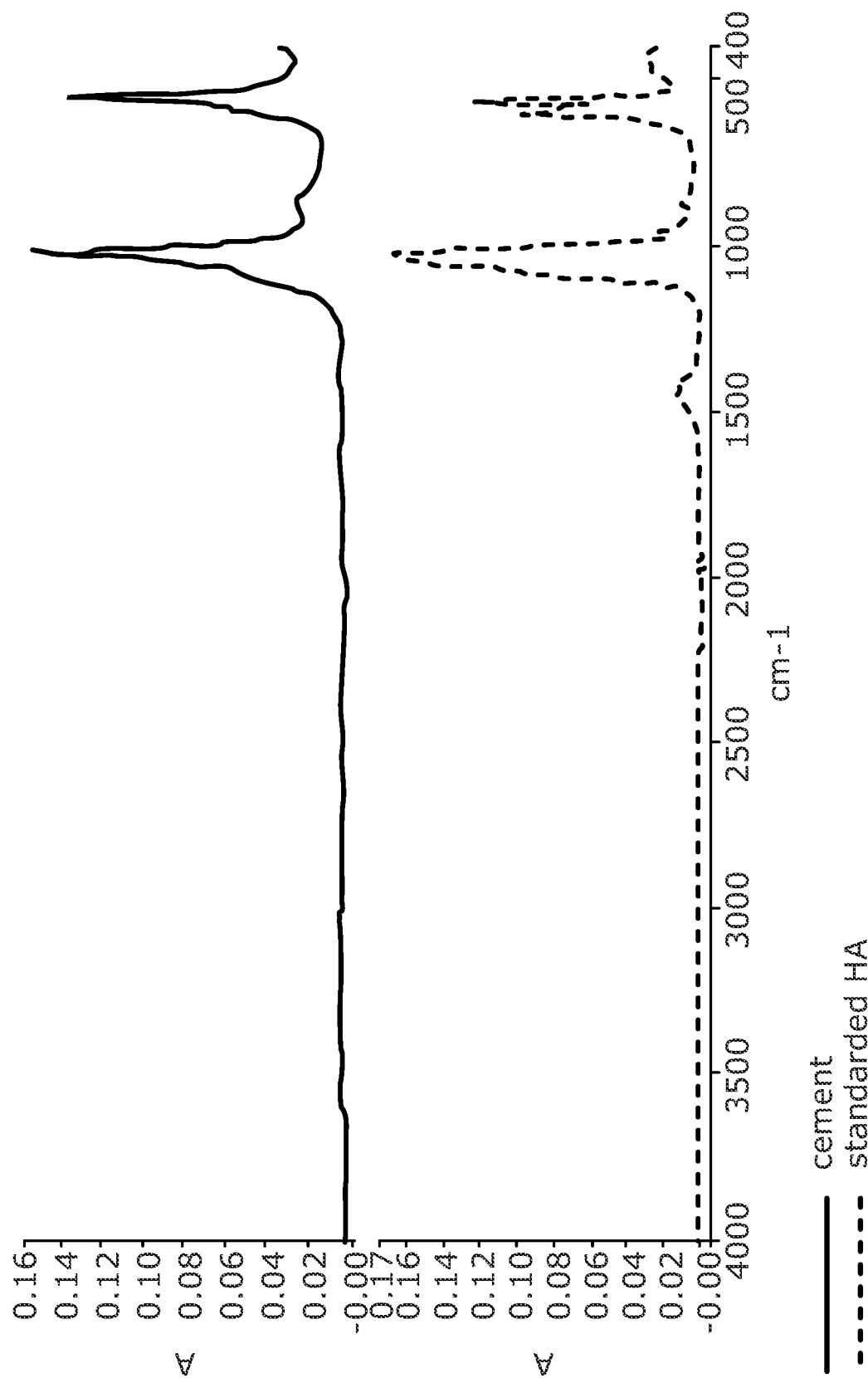
FIG. 4 shows a fourier transform infrared (FTIR) spectrum of a 3D-BGS (red) and a standard hydroxyapatite (HA; black)
Figure 5:
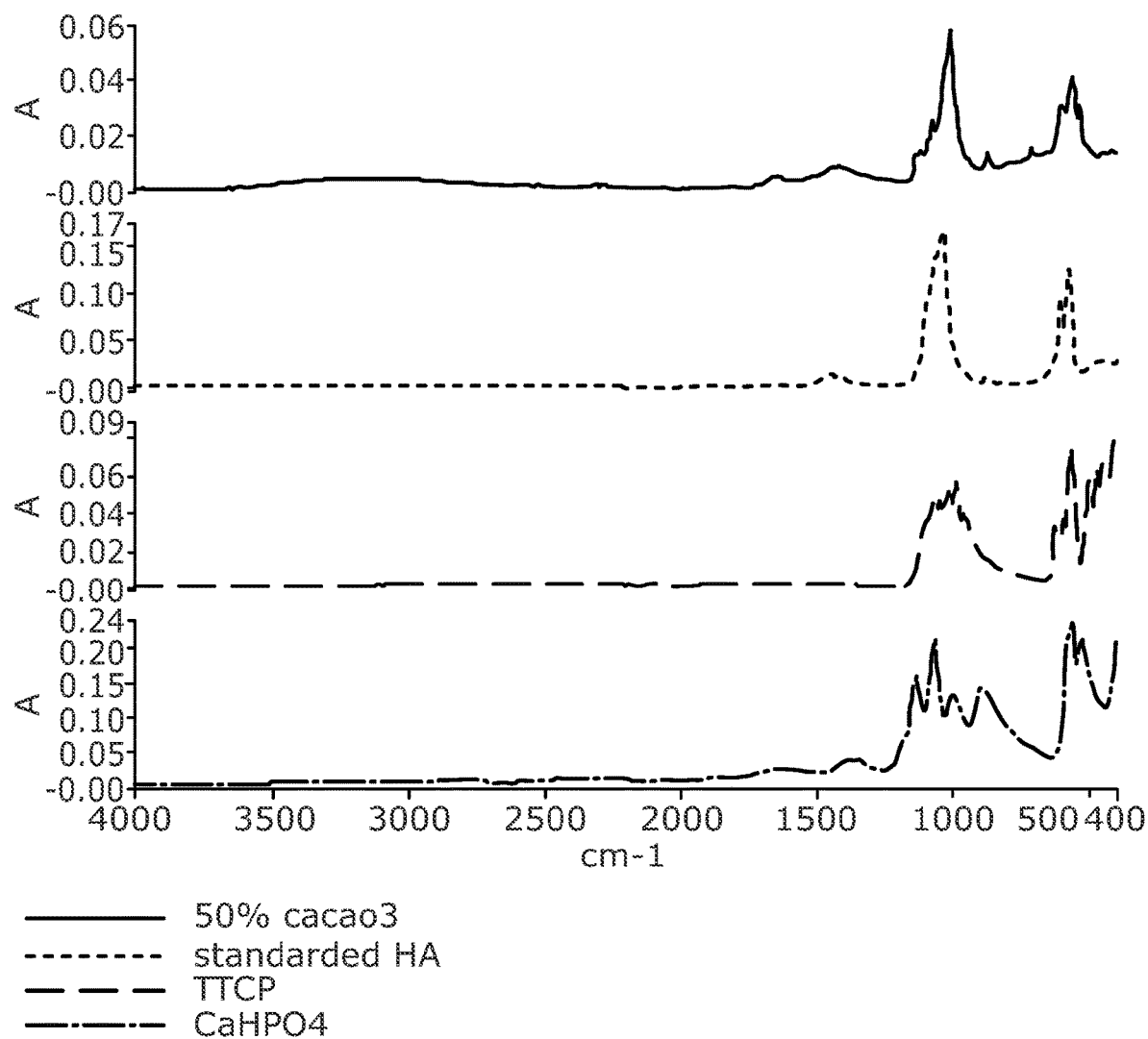
FIG. 5 shows a FTIR spectrum of a 3D-BGS with 50% $CaCO_3$ in powder and soaked in water for 48 hours (black), standard HA (red) TTCP (green) and $CaHPO_4$ (blue)

FTIR 1 mol $TTCP$ and 1 mol $CaHPO_4$ should react in water and form hydroxyapatite. FTIR analysis of grafts is shown FIGS. 4 and 5. The red line shows the spectrum of 3D-BGS and the black line shows the spectrum of standard HA sample. In FIG. 5, the black line shows 3D-BGS with 50% $CaCO_3$ in powder system soaked in water for 48 hours, whilst the red line shows standard HA and green line shows TTCP and blue line shows $CaHPO_4$. The reference samples of FTIR spectrum show absorptions at v1—963 $cm^{-1}$, v3—1036 and 1095 $cm^{-1}$, v4—568 and 600 $cm^{-1}$ are due to $PO_3^{-4}$ ions, $OH^-$ groups lay at 630 $cm^{-1}$. The absorptions at 1061 $cm^{-1}$, 1217 $cm^{-1}$, and 1137 $cm^{-1}$ are due to P=O; the absorptions at 1722 $cm^{-1}$ is due to $HPO_4^-$.

Figure 12:
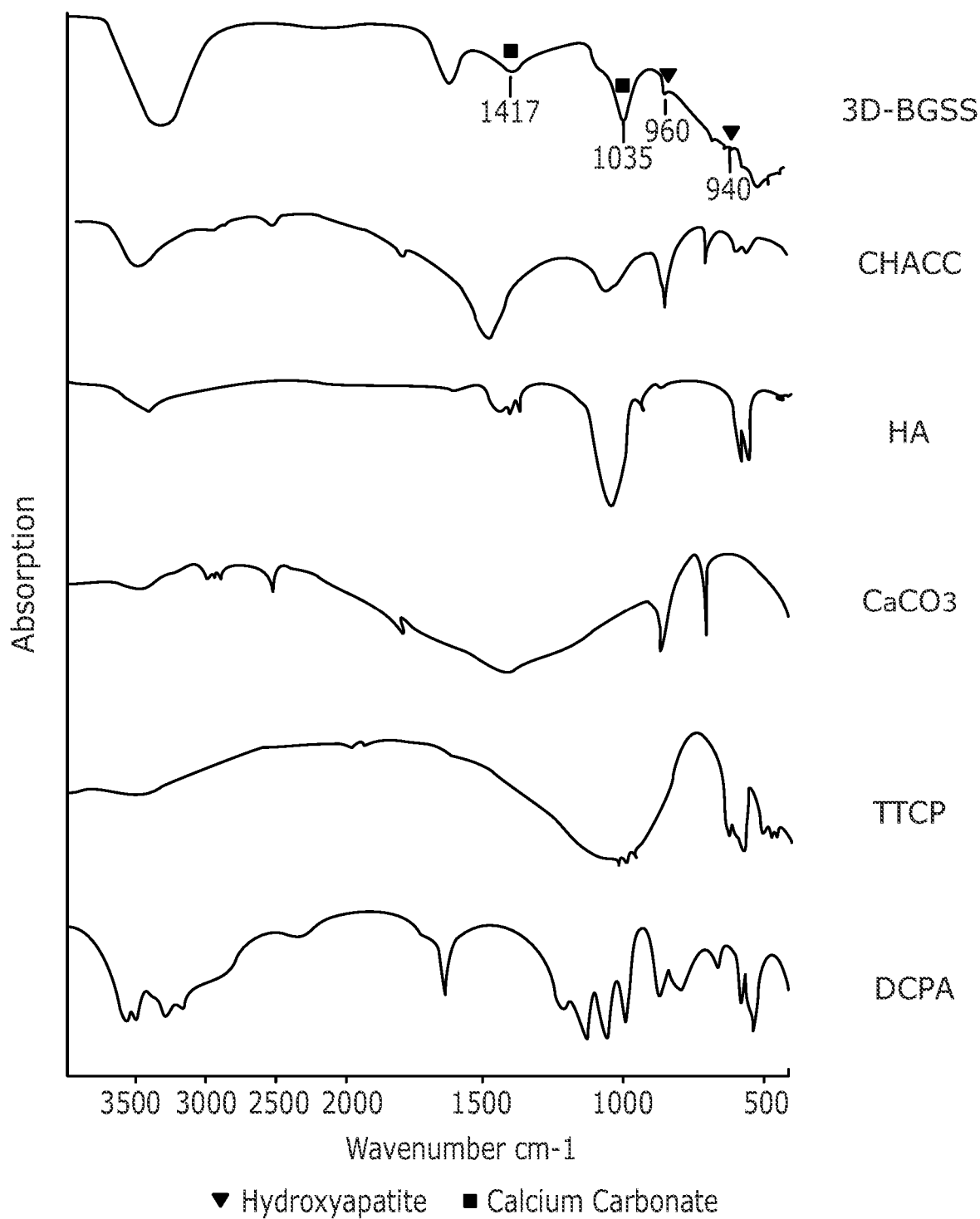
FIG. 12. Comparison of FTIR spectra of HA, CHACC, 3D-BGS and calcium carbonate. The reference samples of FTIR spectrum show absorptions at v1—963 cm$^{-1}$, v3—1036 and 1095 cm$^{-1}$, v4—568 and 600 cm$^{-1}$ are due to $PO_3^{-4}$ ions, $OH^-$ groups lay at 630 cm$^{-1}$. The reference samples of FTIR spectrum show absorptions at v3 peak of 1453.7 cm$^{-1}$, v2 peak of 853.8 cm$^{-1}$, v1 peak of 1083.8 cm$^{-1}$ and v4 peaks of 699.2 and 712.2 cm$^{-1}$ corresponding to $CO_3^{2-}$. Compared with FTIR spectrum of TTCP ($Ca_4(PO_4)_2O$) the strong peak at 1036 and 1417 cm$^{-1}$ was not carried out by TTCP and there is $OH^-$ groups lay at 640 cm$^{-1}$ showed up in FTIR of 3D-BGS which indicates the mixture of TTCP and DCDA has converted to HA. Another strong evidence for the presence of HA is the peak showed up at around 961 cm$^{-1}$. The v4 absorption peak of $CO_3^{2-}$ showed in 3D-BGS, which means there is calcium carbonate remaining in 3D-BGS after all the process. The peaks are all shifted form the reference peaks but in a reasonable value.

In FIG. 12, the reference samples of FTIR spectrum show absorptions at v1—963 $cm^{-1}$, v3—1036 and 1095 $cm^{-1}$, v4—568 and 600 $cm^{-1}$ are due to $PO_3^{-4}$ ions, $OH^-$ groups lay at 630 $cm^{-1}$. The reference samples of FTIR spectrum show absorptions at v3 peak of 1453.7 $cm^{-1}$, v2 peak of 853.8 $cm^{-1}$, v1 peak of 1083.8 $cm^{-1}$ and v4 peaks of 699.2 and 712.2 $cm^{-1}$ corresponding to $CO_3^{2-}$.

Compared with FTIR spectrum of TTCP ($Ca_4(PO_4)_2O$) the strong peak at 1036 and 1417 $cm^{-1}$ was not carried out by TTCP and there is $OH^-$ groups lay at 640 $cm^{-1}$ showed up in FTIR of 3D-BGS which indicates the mixture of TTCP and DCDA has converted to HA. Another strong evidence for the presence of HA is the peak showed up at around 961 $cm^{-1}$. The v4 absorption peak of $CO_3^{2-}$ showed in 3D-BGS, which means there is calcium carbonate remaining in 3D-BGS after all the process. The peaks are all shifted form the reference peaks but in a reasonable value.

Cytotoxicity and Life/Dead Staining

Figure 6:
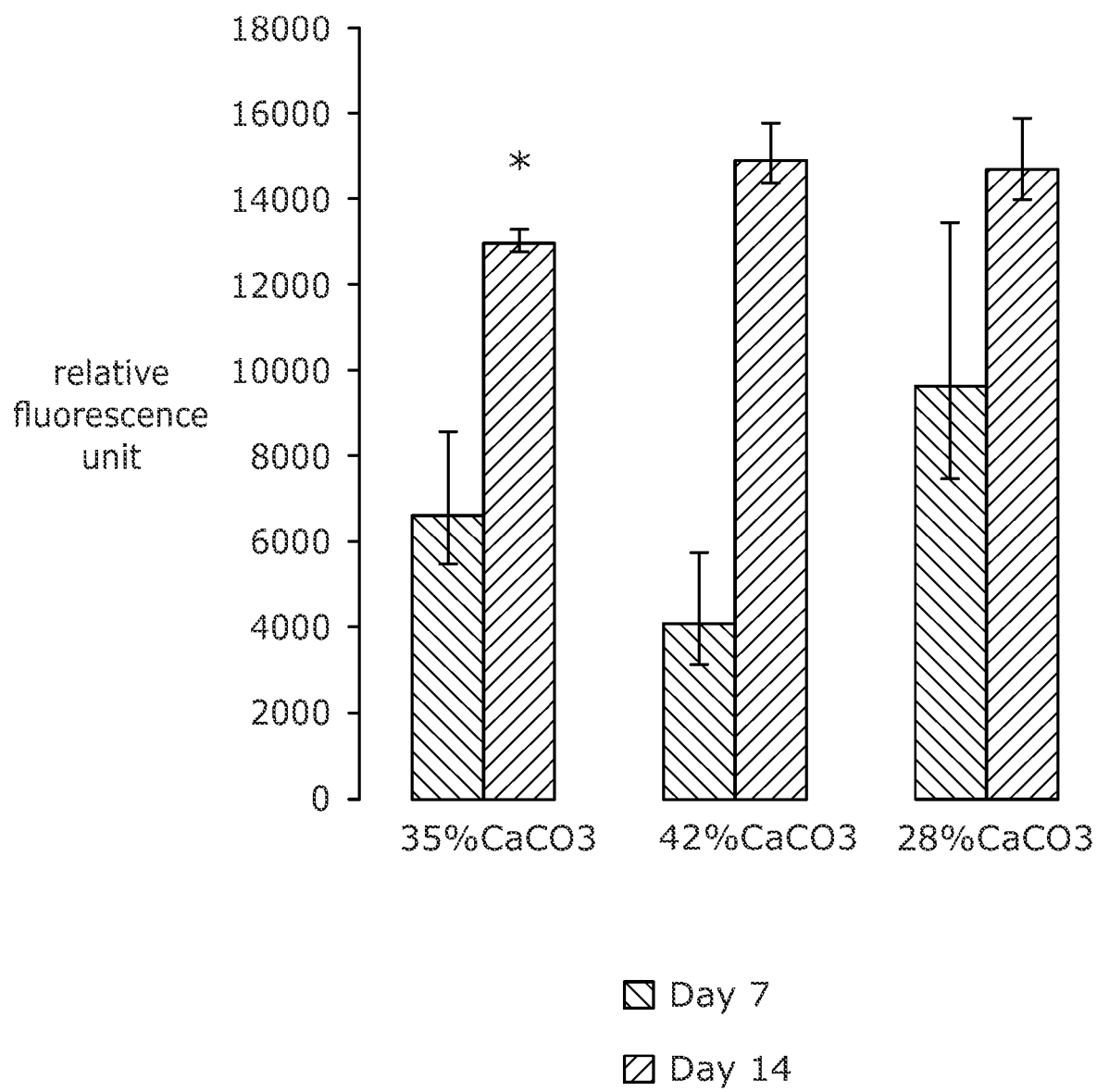
FIG. 6 shows an Alamarblue assay against statistics analysis of 3D-BGS with 35%, 42%, 28% calcium carbonate by weight.
Figure 13:
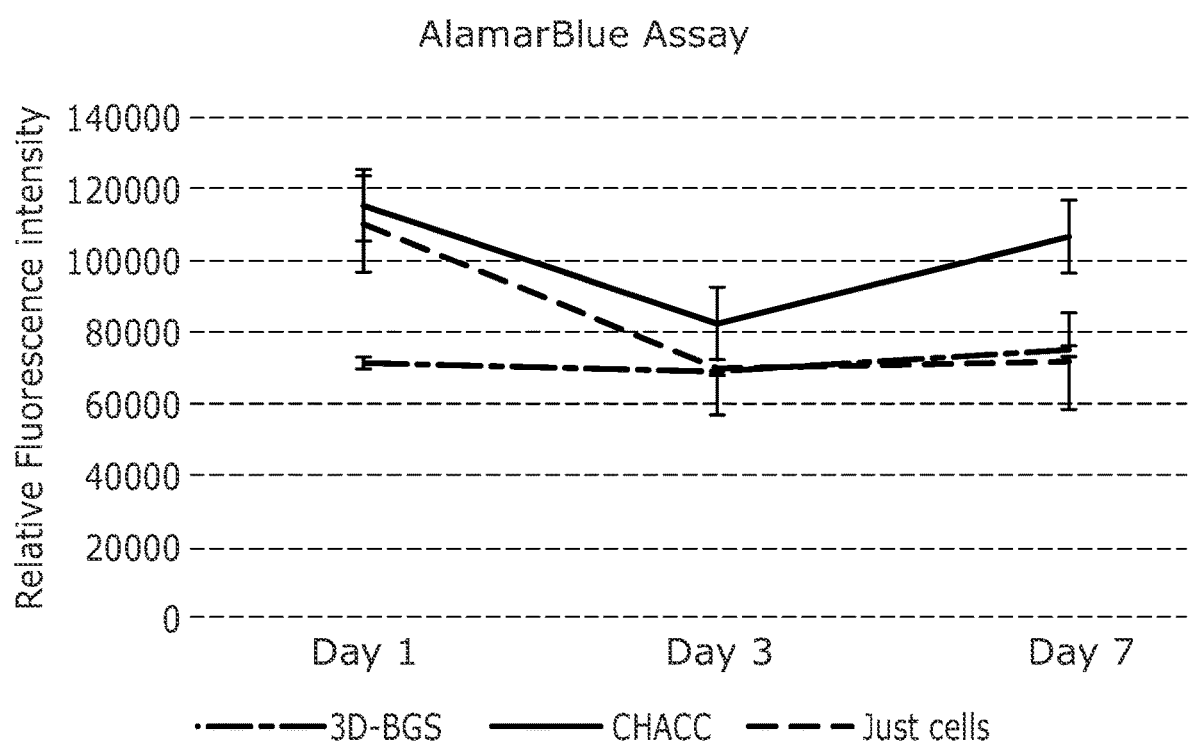
FIG. 13. Alamarblue assay against statistics analysis of 3D-BGS, CHACC and cells only demonstrating 3D-BGS is non-toxic human mesenchymal stem cells.

FIG. 6 show the results of relative fluorescence unit on Alamarblue assay and statistics analysis of hMSC seeded on scaffolds with 35%, 42% and 28% $CaCO_3$ by weight at 7 days and 14 days. There is not much difference between the 3 groups in day 7, but there is a difference between 35% and 42% group in day 14. Compared with day 7 the relative fluorescence units obtained has increased by day 14. FIG. 13 show the results of relative fluorescence unit on Alamarblue assay and statistics analysis of hMSC seeded on 3D-BGS, CHACC and tissue culture plates. Live/Dead staining showed in FIG. 13 indicated that the cell viability was around 92.7±2.8%, which indicates that 3D-BGS is nontoxic to BMSC cells (ISO 10993-5).

Figures 7A, 7B, 7C:
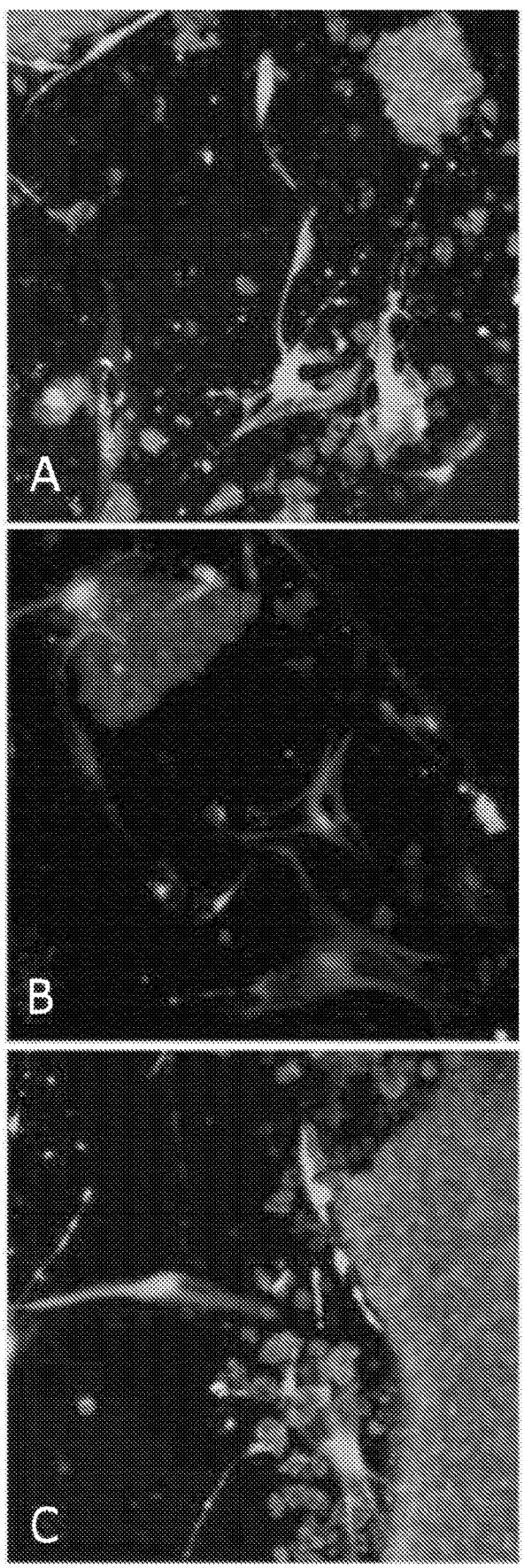
FIGS. 7A-7C show human mesenchymal stem cells (hMSCs) grown on a 3D-BGS scaffold stained with Live/Dead dye. The blue fluorescence shows all the cells, the green fluorescence shows the living cells, the red fluorescence shows the dead cells.
Figure 8A:
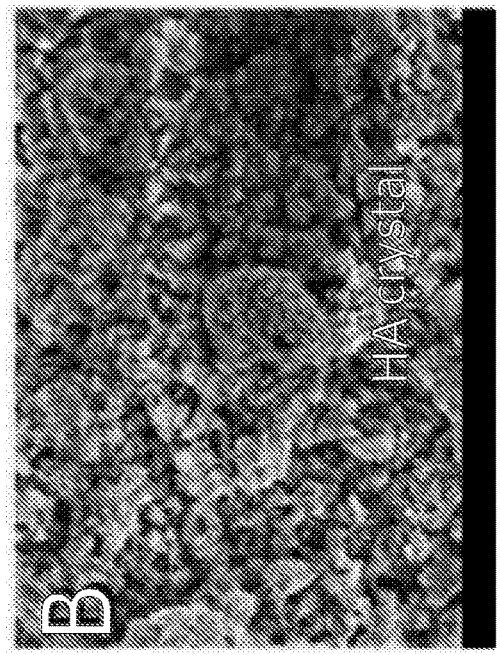
FIGS. 8A-8H. Scanning electron micrograph (SEM) showing the porous structure of the 3D-BGS (FIGS. 8A, 8C), the nano HA crystals on the surface (FIG. 8B) which supports hMSC attachment and growth (FIG. 8D); it is comparable with the porous structure of (FIG. 8E, FIG. 8G), the nano HA crystals on the surface (FIG. 8F) and hMSC attachment and growth (FIG. 8H) on coralline hydroxyapatite/calcium carbonate (CHACC)
Figure 8B:
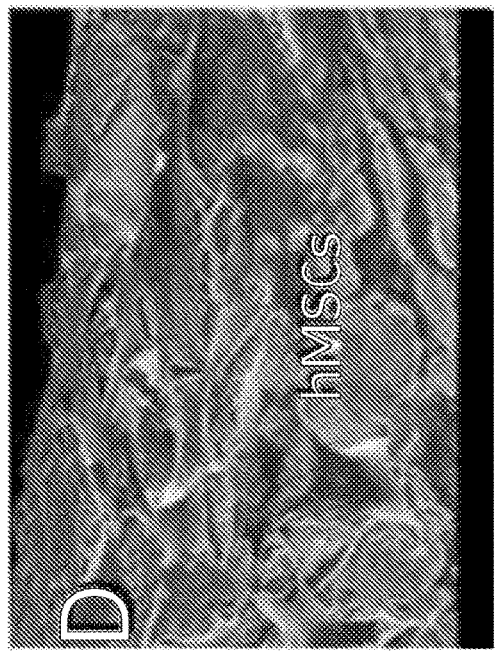
Figure 8C:
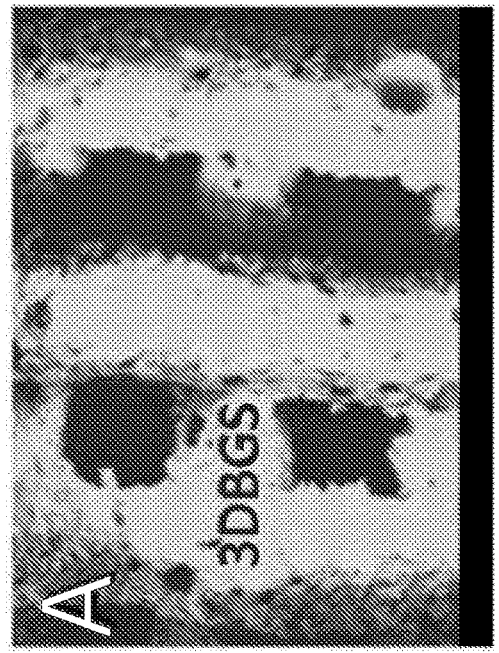
Figure 8D:
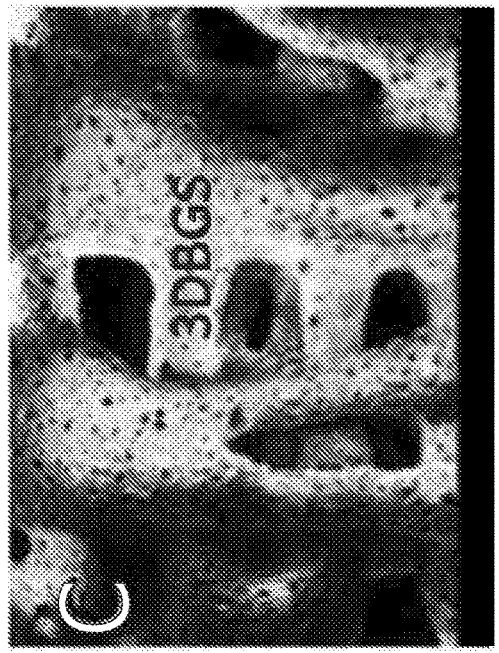
Figure 8E:
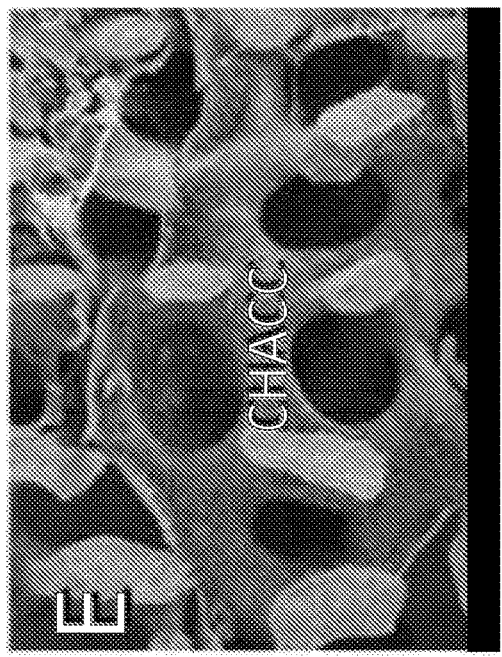
Figure 8F:
Figure 8G:
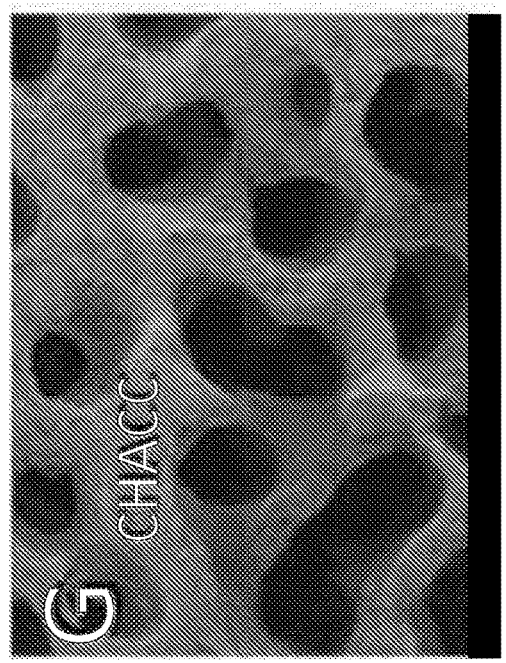
Figure 8H:
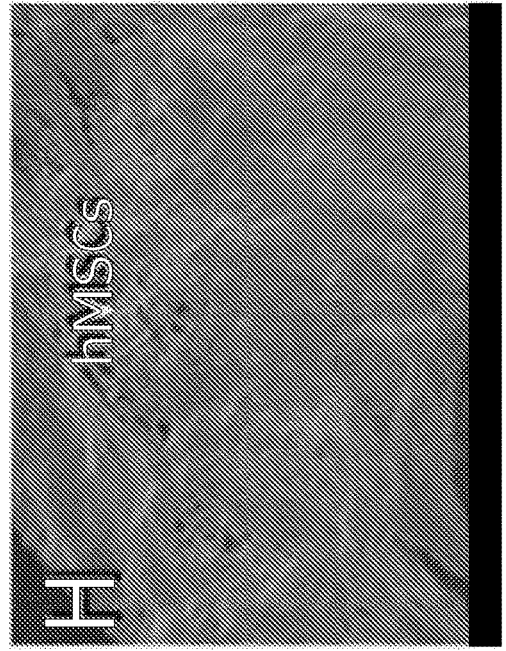
Figure 14:
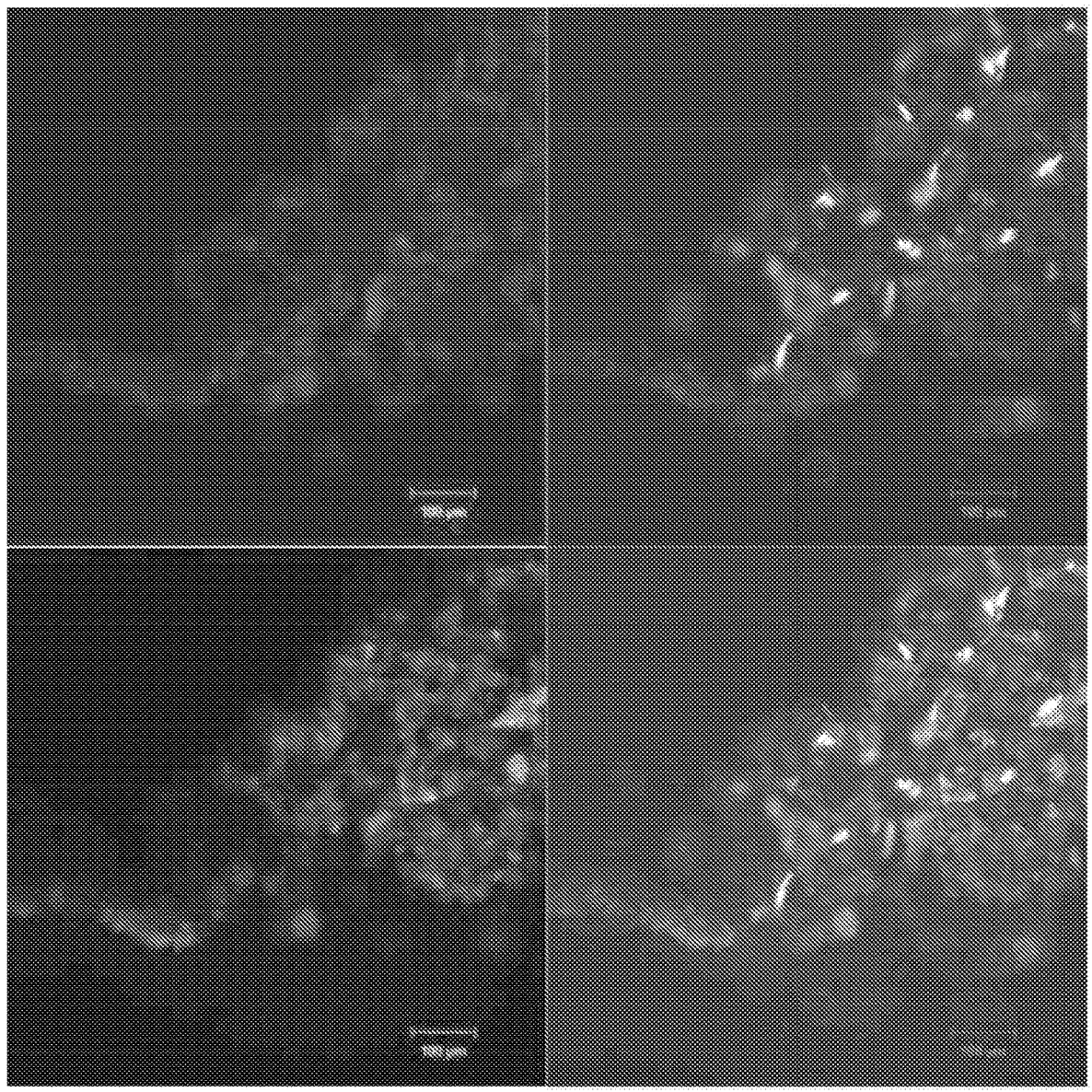
FIG. 14. Human Mesenchymal stem cells (hMSCs) grown on a 3D-BGS scaffold stained with Live/Dead dye. The blue fluorescence shows all the cells, the green fluorescence shows the living cells, the red fluorescence shows the dead cells.

The confocal microscopy of hMSCs stained with Live/Dead dye is shown in FIGS. 7 and 14. The blue fluorescence shows all the cells, the green fluorescence shows the living cells, the red fluorescence shows the dead cells.

SEM micrographs showed the similar porous structure of 3D-BGS (FIG. 8 A and C) and CHACC (FIGS. 8 E and G), the comparable nano HA crystals on the surface of (Fig B and F), and same morphology of hMSC attachment and growth (FIGS. 8. D and H).

Juxtapositional Implantation Between Tibia and Tibialis Anterior Muscle in Rats

The 3D-BGS scaffolds were implanted juxtapositionally between rat tibia and tibialis anterior muscle to observe soft tissue reaction on 3D-BGS in comparison with gelatin sponge. Gelatin is one of additive materials in 3D-BGS.

Figure 9A:
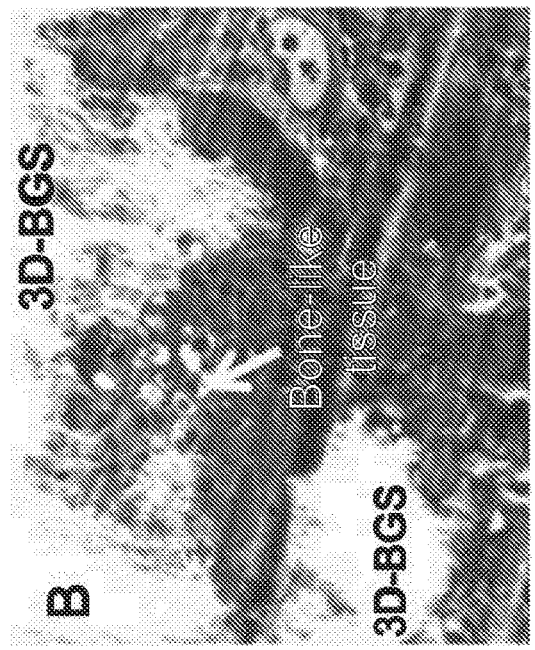
FIGS. 9A-9D. Micrographies of histology of 3D-BGS and collagen sponge implantation into soft tissue between tibia bone and tibialis anterior muscle. By light microscopy, it illustrated that the gelatin sponge implantation (control) resulted in fibrous tissue between tibia and tibialis anterior muscle (FIG. 9A). After 3 weeks of 3D-BGS implantation, the materials were covered by mainly fibroblast, macrophages; interestingly, there were small patches of bone-like tissue formation (FIG. 9B). The TEM observation confirmed the finding by light microscopy, as in control gelatin sponge implantation, macrophagic responses were observed with fibroblast infiltration for tissue regeneration (FIG. 9C); whereas within the patch of bone-like tissue, typical osteocyte-like cells with canaliculi-like structure and within calcified Lacuna were observed (FIG. 9D)
Figure 9B:
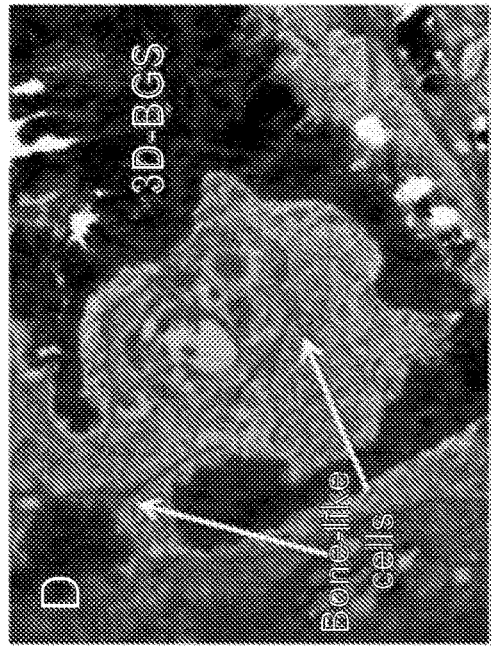
Figure 9C:
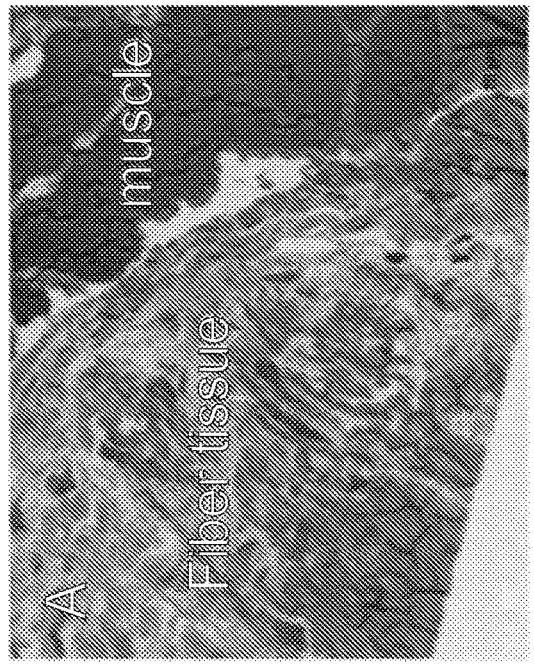
Figure 9D:
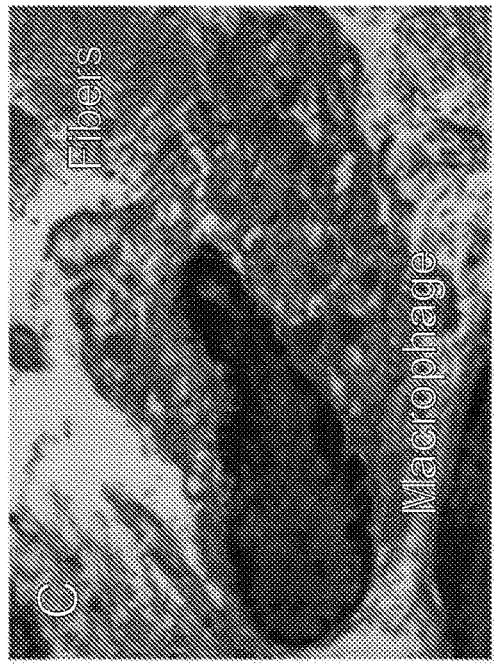
Figure 10A:
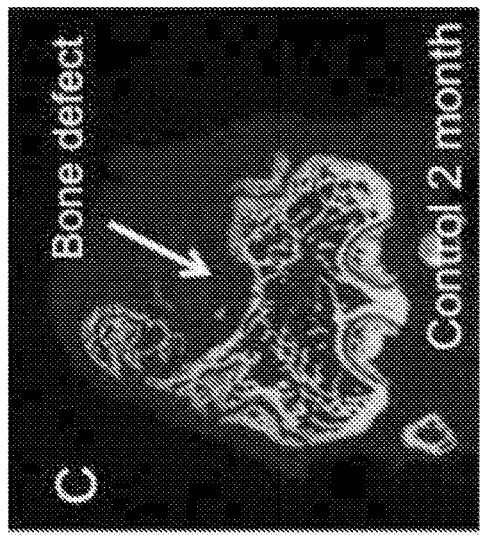
FIGS. 10A-10F. The microCT images illustrated the osteogenic and biodegradation capacity of 3D-BGS on rat femoral bone defects, in comparison with gelatin sponge implantation, at 1 month (FIGS. 10A and 10B), 2 months (FIGS. 10C and 10D) and 3 months (FIGS. 10E and 10F). It is notable that the non-union bone defect in the gelatin sponge implantation (FIGS. 10A, 10C and 10E), and the callus formation surrounding the 3D-BGS (FIG. 10B), the integration of 3D-BGS with trabecular bone formation in bone marrow cavity (FIG. 10D), and the biodegradation and remodelling of the 3D-BS and callus (FIG. 10F).
Figure 10B:
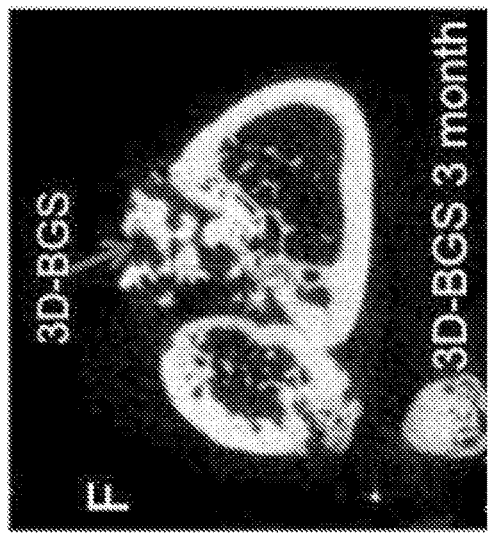
Figure 10C:
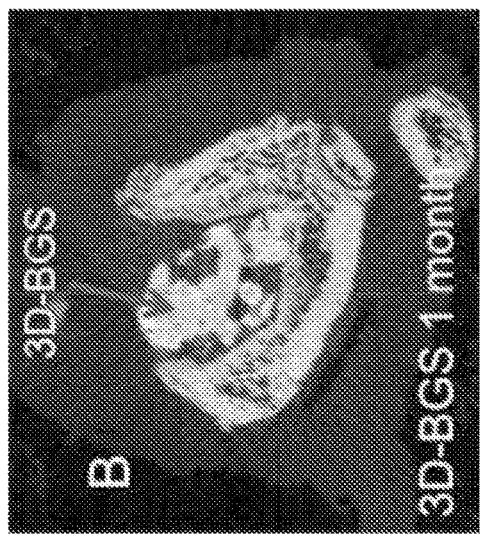
Figure 10D:
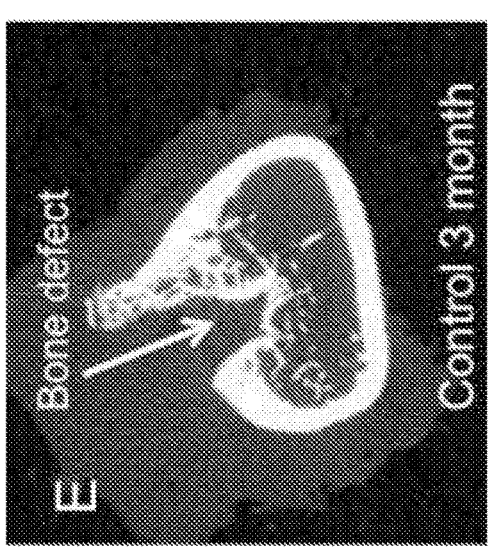
Figure 10E:
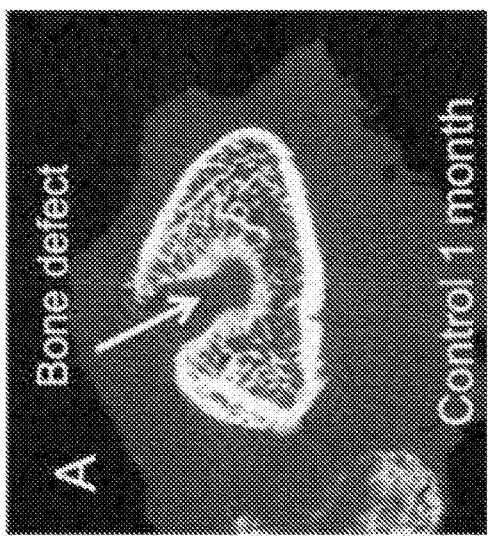
Figure 10F:
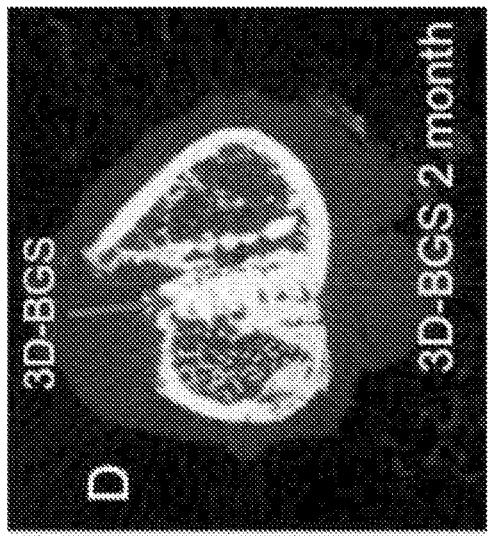

By light microscopy, it illustrated that the gelatin sponge implantation resulted in fibrous tissue formation between tibia and tibialis anterior muscle after 3-weeks implantation (FIG. 9A). In contrast, the 3D-BGS implanted at the same time were covered by mainly connective tissue containing blood vessels, fibroblasts and some macrophages; interestingly, there were small patches of bone-like tissue formation (FIG. 9B). The TEM observation confirmed the finding by light microscopy, as in control gelatin sponge implantation, macrophagic responses were observed with fibroblast infiltration for tissue regeneration (FIG. 9C); whereas within the patch of bone-like tissue in the 3D-BGS group, typical osteocyte-like cells with calcified Lacuna and canaliculi-like structure were observed (FIG. 9D).

Bone Regeneration in Rat Femoral Defect Model

MicroCT scans at 1, 2 and 3 months after gelatin sponge and 3D-BGS implantations are shown in FIG. 10. The ($\varphi$3.5 mm bone defects in gelatin sponge implantation group remained non-union (FIGS. 10 A, C and E). Even though there were reactive callus formation in the bone marrow cavity at 1-month post operation (FIG. 10A), the calluses were remodelled at 2 (FIG. 10C) and 3 months (FIG. 10E). There was extensive callus formation surrounding 3D-BGS to re-union the bone defects healed at 1 month after implantation, though there were some gaps at the material/bone interface (FIG. 10B). At 2 months after implantation, 3D-BGS completely integrated with host compact bone tissue whereas trabecular bone formed within the porous structure of 3D-BGS (FIG. 10D). At 3 months after implantation, large part of 3D-BGS within the bone marrow cavity was degraded via callus remodelling and the remaining 3D-BGS joined the compact bone of the femur (FIG. 10F).

Figure 15:
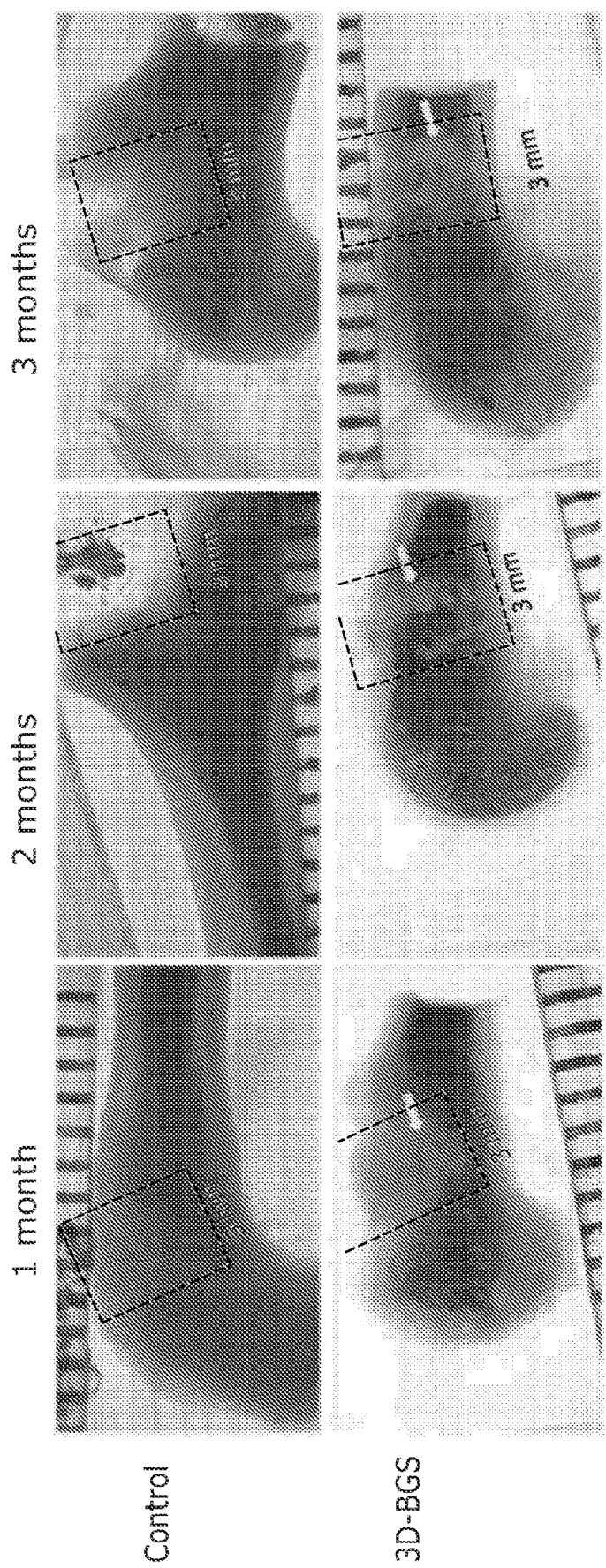
FIG. 15. Gross observation of the effect of 3D-BGS on rat femoral intercondylar bone defect model. Over 3 months the control group showed fibre tissue formation at the bone defect sites whereas in 3D-BGS implantation group there were bone formation surrounding the implants and biodegradation over three months. Arrows indicate the scaffolds.
Figure 16A:
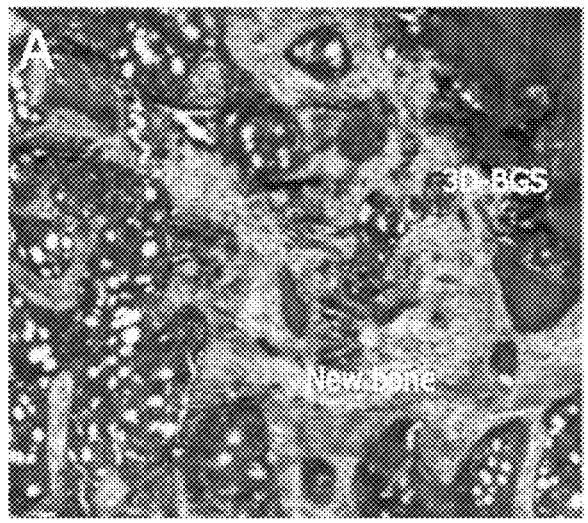
FIGS. 16A-16D. The integration of new bone and 3D-BGS materials illustrated by light and backscatter SEM microscopy at 3 months after implantation.
Figure 16B:
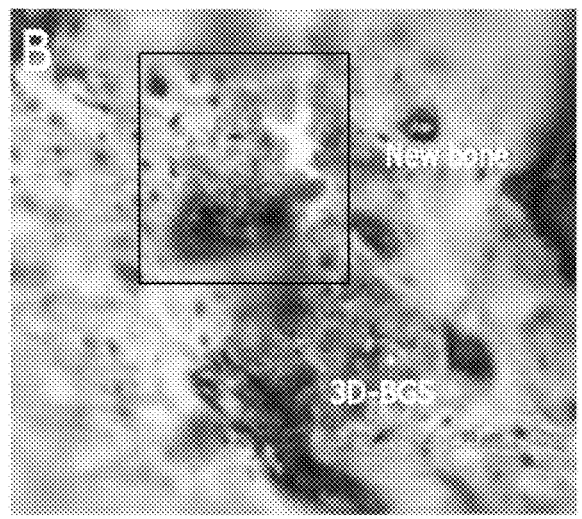
Figure 16C:
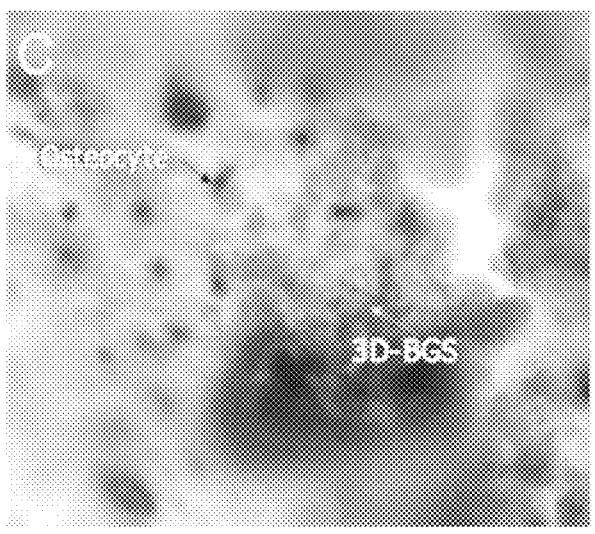
Figure 16D:
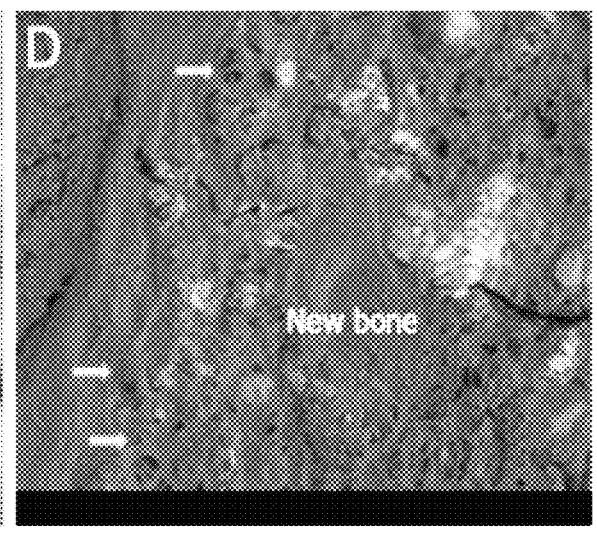

Gross observation of the effect of 3D-BGS on rat femoral intercondylar bone defect model are shown FIG. 15. Over 3 months the control group showed fibre tissue formation at the bone defect sites whereas in 3D-BGS implantation group there were bone formation surrounding the implants and biodegradation over three months. Arrows indicate the scaffolds.

The integration of new bone and 3D-BGS materials illustrated by light and backscatter SEM microscopy at 3 months after implantation are shown in FIG. 16. [A] the dark coloured area shows implanted 3D-BGS, light grey areas are new trabecular bone formation, and the blue areas are toluidine blue stained cells in bone marrow (containing lipid droplets), blood vessels and bone tissue. The 3D-BGS implants are completely integrated and firmly bond to new trabecular bone tissue. The majority of 3D-BGS was degraded and replaced by new bone formation. [B] High magnification of [A] shows a large particle of biodegrading 3D-BGS within new formed trabecular bone tissue. The scattered small Toluidine blue stained dots are osteocytes; whereas the large Toluidine Blue areas are bone marrow (containing lipid droplets) and new blood vessels. [C] High magnification of the marked area in [B]. Toluidine blue stained dots with tails are osteocytes; whereas the large Toluidine Blue area is new blood vessel. [D] The high electron density crystalline showing by backscatter demonstrated where the 3D-BGS particles are. The white arrows indicated osteocytes lacunae. The osteocytes are closely integrated with 3D-BGS.

Figure 17A:
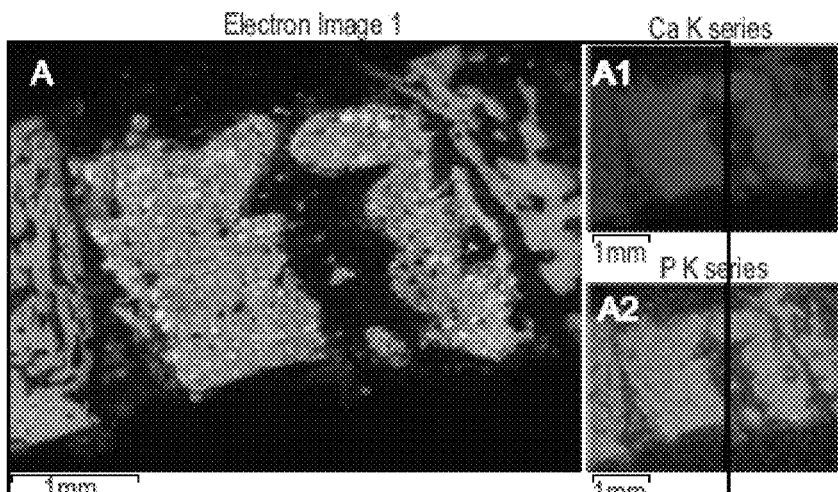
FIGS. 17A-17C. Micro-illustration of SEM backscatter, Energy-dispersive X-ray spectroscopy (EDS) map and element analysis of cross section of 3D-BGS at 1, 2 and 3 months post implantation. The high crystalline areas are 3D-BGS implants in which the areas reduced over three months (FIG. 17A, FIG. 17B, and FIG. 17C). The EDS mapping showed the calcium (A1, B1 and C1) and phosphate (A2, B2, and C2) composition of the implants and bone tissue.
Figure 17B:
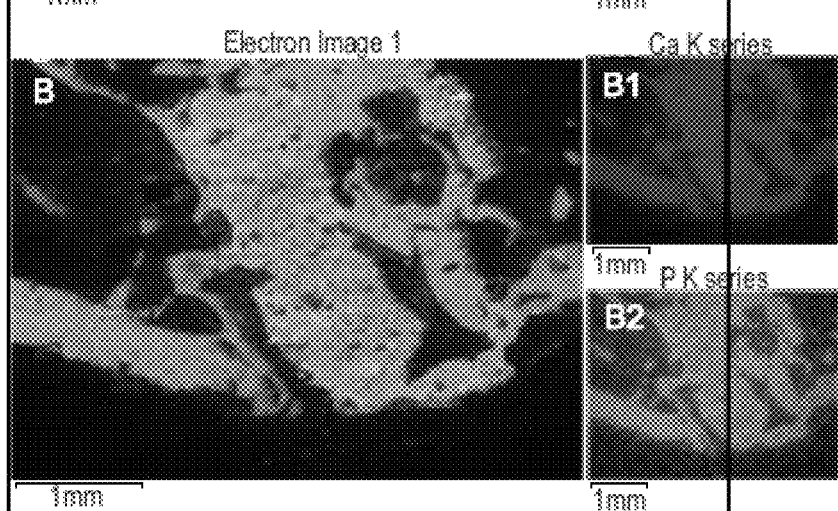
Figure 17C:
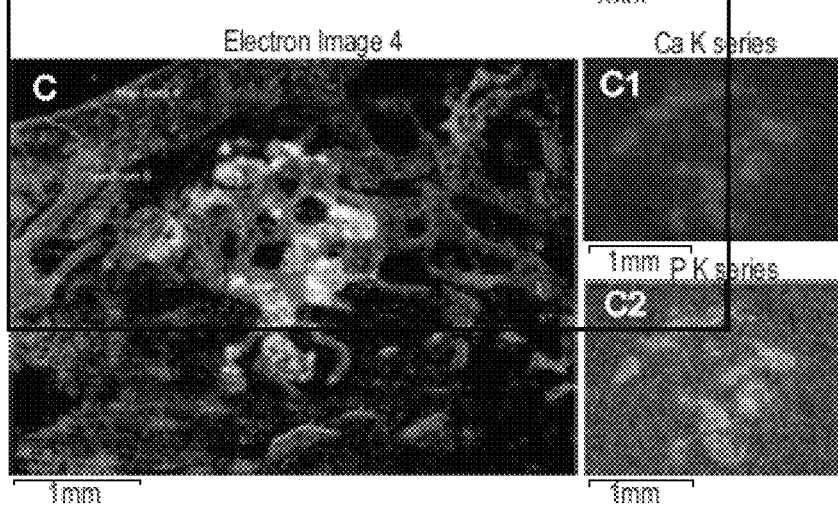

Micro-illustration of SEM backscatter, Energy-dispersive X-ray spectroscopy (EDS) map and element analysis of cross section of 3D-BGS at 1, 2 and 3 months post implantation are shown in FIG. 17. The high crystalline areas are 3D-BGS implants in which the areas reduced over three months (A, B, and C). The EDS mapping showed the calcium (A1, B1 and C1) and phosphate (A2, B2, and C2) composition of the implants and bone tissue.

Figure 18:
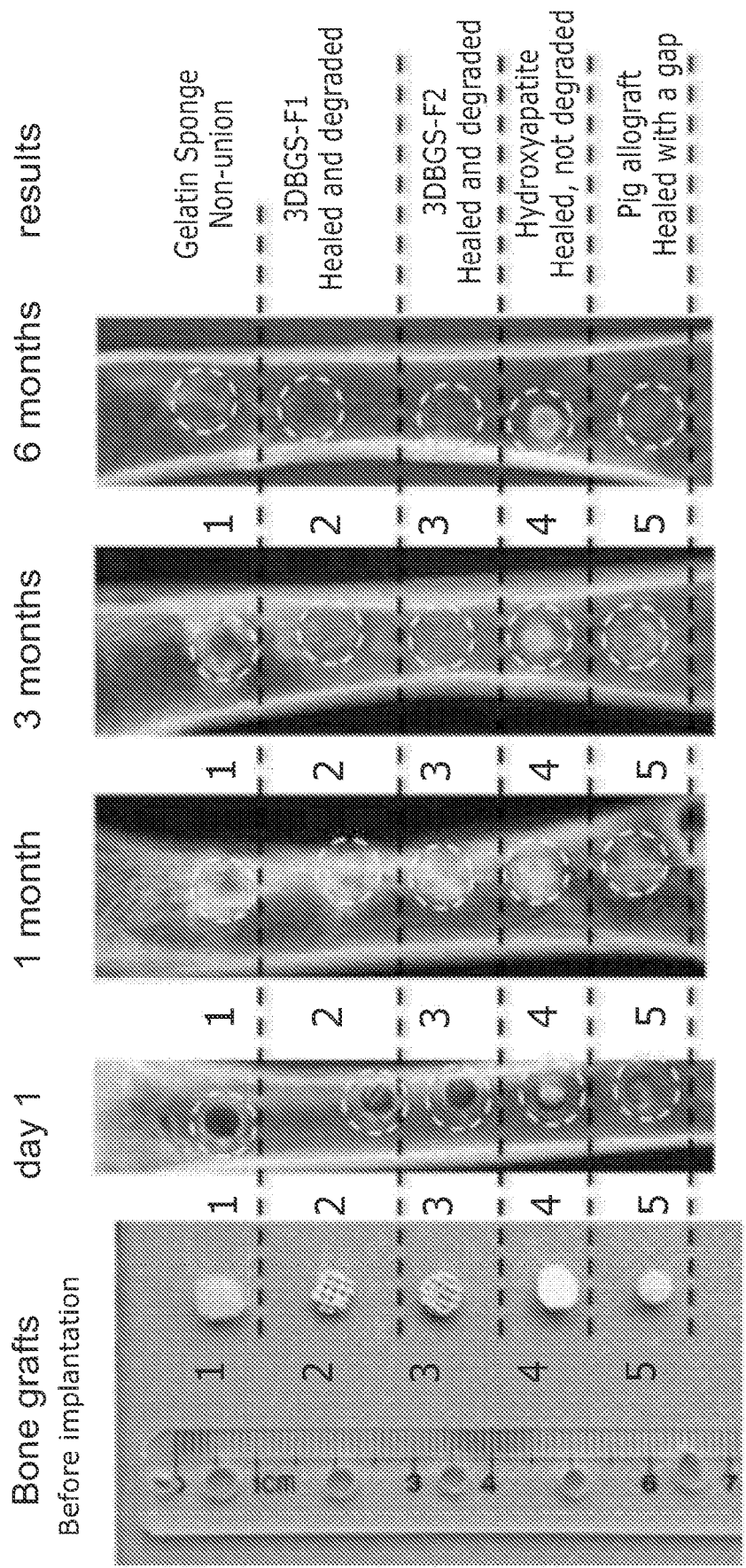
FIG. 18. X-ray radiography illustrated that the comparison of 5 bone graft materials implanted in φ5 mm bone defects of Bama mini pigs at day 1, 1 month, 3 months and 6 months post implantation. There were non-union of Gelatin Sponge (1) implantation between 1 day and 3 months with bone formation in the defects at 6 months. Two 3D-BGS formula implants (2 and 3) were healed with clear sign of biodegradation (similar density to bone without gaps) in 3 months and the defects recovered at 6 months. Pure non-porous hydroxyapatite (4) was healed but not degraded. Swine allograft (5) was healed but there was still gaps in the bone defect area in 3 months but fully recovered at 6 months.

X-ray radiography illustrated that the comparison of 5 bone graft materials implanted in $\varphi$5 mm bone defects of Bama mini pigs at day 1, 1 month, 3 months and 6 months post implantation are shown in FIG. 18. There was non-union of Gelatin Sponge (1) implantation between 1 day and 3 months with bone formation in the defects at 6 months. Two 3D-BGS formula implants (2 and 3) were healed with clear sign of biodegradation (similar density to bone without gaps) in 3 months. Pure non-porous hydroxyapatite (4) was healed but not degraded. Swine allograft (5) was healed but there was still gaps in the bone defect area in 3 months but fully recovered at 6 months.

Summary

We have therefore devised a self-set calcium phosphate/calcium carbonate composition to form a 3D-printed bone graft substitute (3D-BGS) with defined pore size, biocompatibility and controllable biodegradation property. In this study, 3D-BGS was produced and optimised by testing different formulas of compositions to ensure the purged paste had appropriate viscosity and could retain structural integrity after printing. Parameters of printer were adjusted and the biomimetic 3D-BGS with various pore size were fabricated. The products were tested by FTIR spectrum to characterise the composition. The 3D-BGS cytotoxicity was tested by using human mesenchymal stem cells (hMSCs), and further implanted in rat tissue and bone defects to test in vivo biocompatibility, osteogenic capacity and potential biodegradation. Results of FTIR spectrum showed that the 3D-BGS produced by this technique is a mixture of hydroxyapatite (HA) and calcium carbonate (CC). The cytotoxicity test showed that the scaffold is nontoxic and the cells could attach and grow on the material. No infection or adverse tissue reaction were observed after 3D-BGS implantation in comparison to clinically applied gelatin sponge. Interestingly, there were patches of bone-like tissue formation after 3D-BGS implantation juxtapositionally between tibia and tibialis anterior muscle. Callus formation was observed by microCT scanning in 3D-BGS group at 1 month after implantation, followed by full integration with host trabecular and cortical bone at 2 months and biodegradation in bone marrow cavity during the bone remodelling processes at 3 months. However, the same bone defects implanted with gelatin sponge remained non-union until 3 months.

These results supported the strong osteoconductive potential of 3D-BGS. The new formed bone tissue from host at the site of bone defects was firmly integrated into the implants where there were no observable defects left at 2 and 3 months after implantation.

The biodegradation of 3D-BGS was confirmed and the surface area of the implants in bone defects was reduced significantly. It is notable that the implants participated into the bone remodelling process, where it is evident that new bone formation was immediately followed by resorption of implants during the callus remodelling, leaving small islands of implants in large area of new bone formation, in particular at 3 months after implantation in murine model.

The benefit of the porous structure that formed by 3D printing technology is also demonstrated by extensive vascularisation whereby new blood vessels penetrated into the pores to aid bone formation and resorption. The superior results to non-porous HA implants are clearly shown in FIG. 18, while 3D-BGS implanted bone defects were completely healed and the implants were degraded, whilst the non-porous HA implants remained almost unchanged after 6 months post-implantation.

TABLE 1

| Temperature | Pressure | Speed | Platform Temperature |
|---|---|---|---|
| 37° C. | 3 MPa | 50 mm/s | 5° C. |

TABLE 2

| Gelatin concentration | Time | | | | | | |
|---|---|---|---|---|---|---|---|
| | Liquid | Gel | Stand | 0-2 min Out | 2-4 min Out | 4-10 min Out | >10 min Out |
| 10-14% | + | − | − | + | + | + | + |
| 15%-17% | + | + | + | + | + | − | − |
| 18%-19% | + | + | + | + | + | − | − |
| 20-22% | − | + | + | − | − | − | − |
| 22-25% | − | + | + | − | − | − | − |

TABLE 3

| Gelatin concentration | Time | | | | | | |
|---|---|---|---|---|---|---|---|
| | Liquid | Gel | Stand | 0-2 min Out | 2-4 min Out | 4-10 min Out | >10 min Out |
| 10-14% | + | − | − | + | + | + | + |
| 15%-17% | + | + | + | + | + | + | − |
| 18%-19% | + | + | + | + | + | + | − |
| 20-22% | − | + | + | + | + | − | − |
| 22-25% | − | + | + | + | − | − | − |

TABLE 4

| Gelatin concentration | Time | | | | | | |
|---|---|---|---|---|---|---|---|
| | Liquid | Gel | Stand | 0-2 min Out | 2-4 min Out | 4-10 min Out | >10 min Out |
| 10-14% | + | − | − | + | + | + | + |
| 15%-17% | + | − | − | + | + | + | + |
| 18%-19% | + | − | − | + | + | + | − |
| 20-22% | + | + | + | + | + | − | − |
| 22-25% | + | + | + | + | − | − | − |

TABLE 5

| Gelatin Percentage by weight | Temperature | | | | | | | |
|---|---|---|---|---|---|---|---|---|
| | RT | | 32° C. | | 37° C. | | 42° C. | |
| | Out | Stand | Out | Stand | Out | Stand | Out | Stand |
| 30% | − | − | − | − | + | + | + | + |
| 33% | + | − | + | + | + | + | + | − |
| 36% | + | + | + | + | + | + | + | − |
| 39% | + | − | + | − | + | − | + | − |

TABLE 6

| Component | $CaCO_3$ | $CaHPO_4$ | TTCP | Gelatin Solvent (15%) |
|---|---|---|---|---|
| Weight by percentage | 28 | 16.3 | 25.7 | 30 |

TABLE 7

| Period | 1 month | 2 months | 3 months |
|---|---|---|---|
| Percentage (%) | 31.9 ± 1.6 | 12.6 ± 0.7* | 8.1 ± 0.6* |

ABBREVIATIONS

3D-BGS 3D-printed bone graft substitute
CC calcium carbonate
CDHP calcium dihydrogenphosphate,
CHACC coralline hydroxyapatite/calcium carbonate
CPC calcium phosphate cement
DCP dicalcium phosphate dihydrate ($CaHPO_4 \cdot 2H_2O$)
EPS Energy-dispersive X-ray spectroscopy
FTIR Fourier Transform Infrared Spectroscopy
HA hydroxyapatite
hMSCs human Mesenchymal Stem Cells
OCP Octacalcium phosphate
SBF simulated body fluid
SLS selective laser sintering
TCP Tricalcium phosphate
TTCP tetracalcium phosphate Calcium phosphate

The invention claimed is:

1. A printing method for making a synthetic, biodegradable, bone graft substitute comprising:
   (a) mixing calcium carbonate with a binding material to provide a powdered mixture, wherein the binding material comprises tetracalcium phosphate ($Ca_4(PO_4)_2O$; TTCP) and calcium hydrogen phosphate ($CaHPO_4$) that react in the presence of gelatin to provide a cement or slurry, wherein the calcium carbonate is provided in the range 20-40% by weight of the cement or slurry;
   (b) mixing the powdered mixture of part (a) with gelatin to make a cement or slurry, wherein said gelatin is provided in a solution in an amount of 30-36% by weight of the cement or slurry;
   (c) wherein the mixing in step (a), and/or step (b) is undertaken at 25° C. to 40° C.; and
   (d) printing a three-dimensional bone graft substitute (3D-BGS) from the cement or slurry of part (b) onto a platform using a three-dimensional printer, wherein the temperature of the platform is 2.5° C.-10° ° C.

2. The method according to claim 1, wherein the calcium carbonate is provided as a powder.

3. The method according to claim 1, wherein the calcium carbonate is in the form of nanoparticles or microparticles.

4. The method according to claim 3, wherein the nanoparticles are in the range of about 10-999 nm in diameter; and the microparticles are in the range of 1-30 μm.

5. The method according to claim 1, wherein the binding material comprising the combination of TTCP and $CaHPO_4$ are in the range 10-50% by weight of the cement.

6. The method according to claim 5 wherein the combination of TTCP and CaHPO4 are provided in solid form and are mixed and ground together in the relative amounts wherein the ratio of the TTCP to the CaHPO4 is a range of about 0.5:1 to 5.5:1.

7. The method according to claim 1, wherein part (a) further comprises mixing of an additive, wherein said additive is any compound that affects viscosity and so ensures the mixed product has suitable fluidity to flow but not so much that it fails to hold shape when printed.

8. The method according to claim 1, wherein the printing of step (d)
- comprises depositing the mixture from step (b) layer by layer to produce 3D-BGS wherein each layer is ideally deposited at an angle with respect to the preceding layer to generate a porous structure;
- is controlled to produce desired pore sizes in the 3D-BGS product wherein said pore sizes are selected according to the intended use; and/or
- further comprises printing onto a substrate comprising a support material wherein said cement is deposited in a manner such that said support material is incorporated, partially or fully, into the 3D-BGS.

9. The method according to claim 1, further comprising incorporating an active agent into the cement, slurry or product prior to or following the printing step.

10. A mixture for making a three-dimensional bone graft scaffold comprising:
i) calcium carbonate in the range of 20-40% by weight of the mixture;
ii) a binding material wherein the binding material comprises tetracalcium phosphate ($Ca_4(PO_4)_2O$; TTCP) and calcium hydrogen phosphate ($CaHPO_4$) that react in the presence of gelatin to provide a cement or slurry; and
iii) gelatin provided in a solution at a concentration whereby the amount of gelatin when in the mixture is in the range of 30-36% by weight of the mixture wherein the mixture is generated using the mixing steps of claim 1.

* * * * *